United States Patent [19]

Kabal

[11] Patent Number: 5,743,268
[45] Date of Patent: Apr. 28, 1998

[54] NONINVASIVE HEMODYNAMIC ANALYZER ALTERABLE TO A CONTINUOUS INVASIVE HEMODYNAMIC MONITOR

[76] Inventor: John Kabal, 1142 Walker Rd., Ste. D, Great Falls, Va. 22066

[21] Appl. No.: 548,513

[22] Filed: Apr. 11, 1995

Related U.S. Application Data

[63] Continuation of Ser. No. 314,732, Oct. 3, 1994, abandoned, which is a continuation-in-part of Ser. No. 140,453, Oct. 25, 1993, Pat. No. 5,584,298.

[51] Int. Cl.$^6$ .................................................. A61B 5/00
[52] U.S. Cl. .......................... 128/691; 128/713; 128/748; 128/668
[58] Field of Search .................. 128/668, 670.1, 128/691.2, 713, 748, 695

[56] References Cited

U.S. PATENT DOCUMENTS

| | | | |
|---|---|---|---|
| 5,031,629 | 7/1991 | DeMarzo | 128/670 |
| 5,103,828 | 4/1992 | Sramek | 128/713 |
| 5,241,966 | 9/1993 | Finkelstein et al. | 128/713 |
| 5,265,615 | 11/1993 | Frank et al. | 128/713 |
| 5,316,004 | 5/1994 | Chesney et al. | 128/668 |

*Primary Examiner*—Robert L. Nasser
*Attorney, Agent, or Firm*—Sixbey Friedman Leedom & Ferguson; Evan R. Smith

[57] ABSTRACT

A noninvasive method for calculating Actual Stroke Volume and Cardiac Output of a human heart uses computerized algorithms, and is implemented in a continuous noninvasive hemodynamic analyzer which computes a complete real-time Hemodynamic Profile with 12 parameters, in both rest and exercise modes. Inputs are received noninvasively by the analyzer, and a cascade of algorithms are used to calculate Stroke Volume, Ejection Fraction and Acceleration Index in Rest and Exercise. The analyzer displays or prints a summary in graphical form.

16 Claims, 21 Drawing Sheets

— Ideal Supply/Demand  ○ Supine  ■ Upright

□ Supine  ■ Upright  ▫ Cold  • Hyperventil.

FIG. 17

INPUTS:    PARAMETERS 9 OBLIGATORY            2 OPTIONAL

 

INTERMEDIARY PARAMETERS:   parameters are calculated by computer

+ IDEAL VALUES OF ALL INTERMEDIARY AND FINAL HEMODYNAMIC PARAMETERS

FINAL PARAMETERS:   are presented on computer screen or printed out

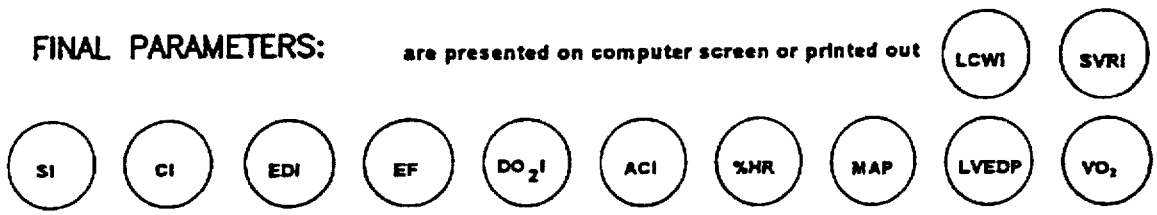

A=Age
ACI=Acceleration Index
BSA=Body Surface Area
CI=Cardiac Index
D=Date
DBP=Diastolic Blood Pressure
DoB=Date of Birth
$DO_2I=O_2$ Delivery Index
LVEDP = Left Ventricular End Diastolic Pressure
$VO_2$= Maximal Oxygen Consumption EDI=End Diastolic Index
EF=Ejection Fraction
H=Height
Hgb==Hemoglobin
HR=Heart Rate
HR-R=Heart Rate-Ratio
%HR=% Heart Rate
LCWI=Left Cardiac Work Index MAP=Mean Arterial Blood Pressure
PP=Pulse Pressure
PP-R=Pulse Pressure Ratio
S=Sex
$SaO_2=O_2$ Saturation of Arterial Blood
SBP=Systolic Blood Pressure
SI=Stroke Index
SVRI=Systemic Vascular Resistance Index
W=Body Weight △ = Obligatory & Optional Parameters(Inputs)
☐ = Intermediary Parameters
◯ = Final Parameters

FIG. 18

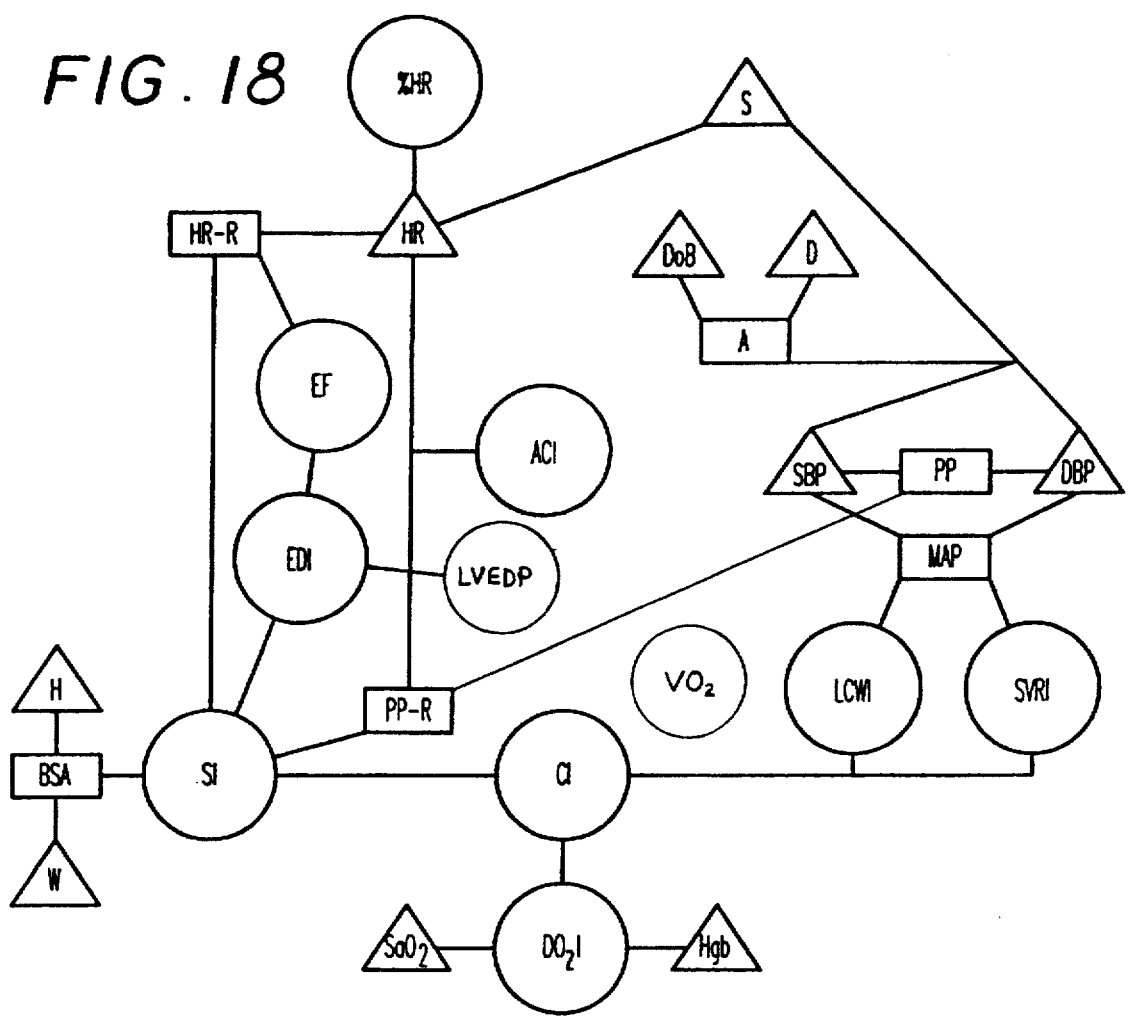

A=Age
ACI=Acceleration Index
BSA=Body Surface Area
CI=Cardiac Index
D=Date
DBP=Diastolic Blood Pressure
DoB=Date of Birth
$DO_2I=O_2$ Delivery Index $VO_2$ = Maximal Oxygen Consumption LVEDP = Left Ventricular End Diastolic Pressure EDI=End Diastolic Index
EF=Ejection Fraction
H=Height
Hgb==Hemoglobin
HR=Heart Rate
HR-R=Heart Rate-Ration
%HR=% Heart Rate
LCWI=Left Cardiac Work Index MAP=Mean Arterial Blood Pressure
PP=Pulse Pressure
PP-R=Pulse Pressure Ratio
S=Sex
$SaO_2=O_2$ Saturation of Arterial Blood
SBP=Systolic Blood Pressure
SI=Stroke Index
SVRI=Systemic Vascular Resistance Index
W=Body Weight △ = Obligatory & Optional Parameters(Inputs)

☐ = Intermediary Parameters

◯ = Final Parameters

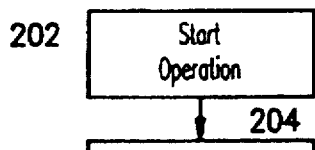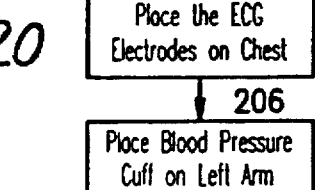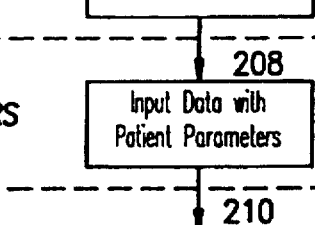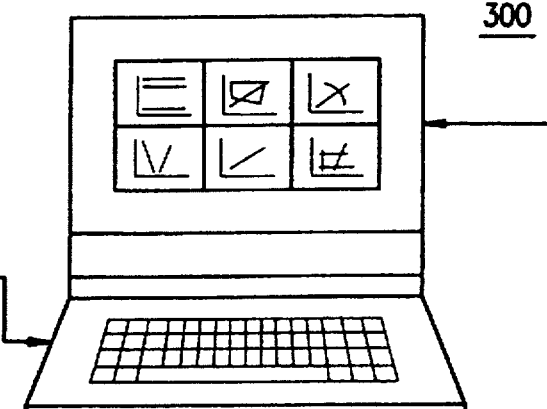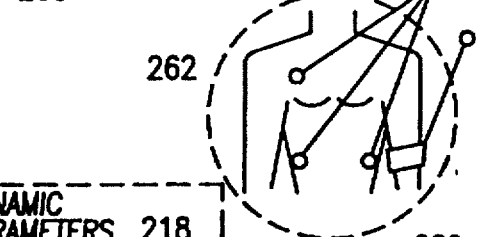
FIG. 20

FIG. 22
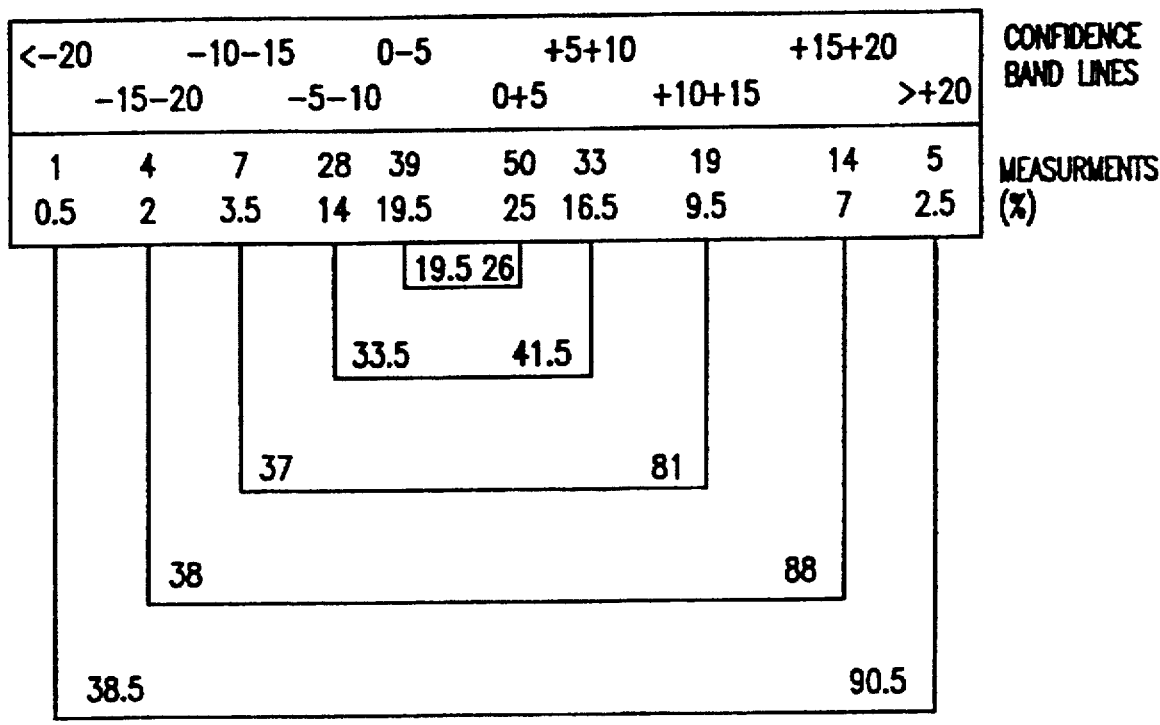
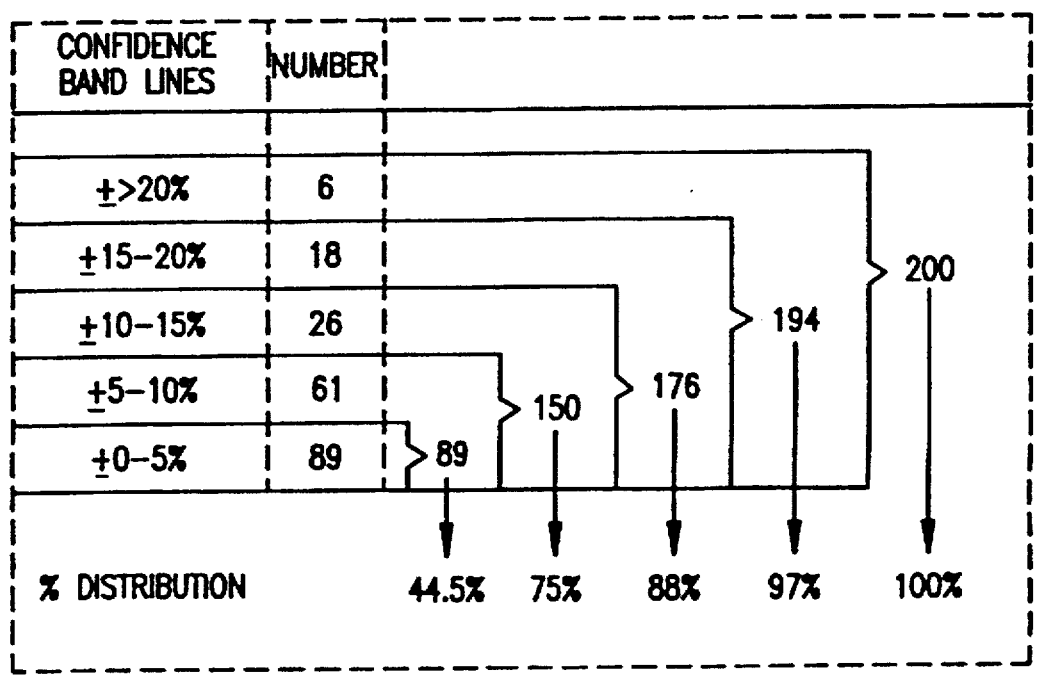

```
• Name:  D., L         # : 2436         Race: Caucasian    Height in. :    68.5
• DoB :  03/30/44      Date : 12/02/88   Marital S : M     Weight lbs :    162.0
• Age :  44.7 year old Sex : M           BMI : 24          Over/under in % : -2.0
```

DIAGNOSTIC DIRECTIONS of the HEMODYNAMIC ANALYSIS    Supine Position

```
                              <
                             MAP
                              .
           =      =     =    =     =     =    < .
         LVEDP   LVEDI  %EF   CI   ACI   SI    HR
                              . . .
         . . . . . . . . . .  VO2   . . . . . . . . .
                        .   =   .
                            SVRI
              =O2DI         =         LCWI=
```

| PARAMETERS | Normal Ranges | Actual Values | DIAGNOSES |
|---|---|---|---|
| TENSION<br>Mean Arterial Blood Pressure : MAP | 84-100<br>mmHg | 82 | HYPOTENSION |
| DYNAMIA        (CO= 6.837 ml/min)<br>Cardiac Index : CI | 2.8 - 4.2<br>L/min/m2 | 3.6 | NORMODYNAMIA |
| AFTERLOAD : SVRI<br>Syst.Vasc.Resist. | 1660-2580<br>dyn.sec/cm5/m2 | 1795 | NORMO-VASOACTIVITY |
| EJECTION LOAD<br>Stroke Index : SI | 30-65<br>ml/min/m2 | 58 | NORMAOEJECTION |
| EFFICIENCY RATIO(LV)<br>Ejection Fraction : % EF | 50-65<br>% | 57 | NORMOEFFICIENCY |
| INOTROPY<br>ACCELERATION INDEX : ACI | 0.7-1.5 sec-2 | 1.0 | NORMOINOTROPY |
| CHRONOTROPY<br>Heart Rate and/or % Max.Heart Rate | 37-43<br>% of Max.HR | 35 | HYPOCHRONOTROPY |
| PRELOAD = VOLEMIA<br>End Diastolic Index : EDI | 60-110<br>ml/min/m2 | 101 | NORMOVOLEMIA |
| MYOCARD.O2 CONSUMP.<br>Left Cardiac Work Index : LCWI | 3.3-5.3<br>kg/m.m2 | 4.0 | NORMOCAPACITY |
| TOTAL O2 DELIVERY<br>Oxygen Delivery Index : O2DI | 570-795<br>ml/min/m2 | 755 | NORMO-O2-DELIVERY |

FIG. 23A

```
* * * * * * * * * * * * * * * * * * * * * * * * * * * * * * * * * * * * * * * * * * * * * * * * * *
* Name:  D., L              #: 2436        Race: Caucasian    Height in. :      68.5            *
* DoB :  03/30/44           Date : 12/02/88 Marital S : M     Weight lbs :      162.0           *
* Age :  44.7 year old      Sex : M         BMI : 24          Over/under in % : -2.0            *
* * * * * * * * * * * * * * * * * * * * * * * * * * * * * * * * * * * * * * * * * * * * * * * * * *
*           DIAGNOSTIC DIRECTIONS of the HEMODYNAMIC ANALYSIS    Upright Position              *
* * * * * * * * * * * * * * * * * * * * * * * * * * * * * * * * * * * * * * * * * * * * * * * * * *
```

$$\begin{array}{c} < \\ MAP \\ \cdot \\ = \quad = \quad = \quad = \quad = \quad < \\ LVEDP \cdot \cdot LVEDI \cdot \cdot \%EF \cdot \cdot \cdot CI \cdot \cdot \cdot ACI \cdot \cdot \cdot SI \cdot \cdot \cdot HR \\ \cdot \cdot \cdot \\ \cdot VO2 \cdot \\ = \\ SVRI \\ =O2DI \quad = \quad LCWI= \end{array}$$

| PARAMETERS | Normal Ranges | Actual Values | DIAGNOSES |
|---|---|---|---|
| TENSION<br>Mean Arterial Blood Pressure : MAP | 84-100<br>mmHg | 90 | NORMOTENSION |
| DYNAMIA    (CO= 5.473 ml/min)<br>Cardiac Index : CI | 2.8 - 4.2<br>L/min/m2 | 2.9 | NORMODYNAMIA |
| AFTERLOAD : SVRI<br>Syst.Vasc.Resist. | 1660-2580<br>dyn.sec/cm5/m2 | 2462 | NORMO-VASOACTIVITY |
| EJECTION LOAD<br>Stroke Index : SI | 30-65<br>ml/min/m2 | 46 | NORMAOEJECTION |
| EFFICIENCY RATIO(LV)<br>Ejection Fraction : % EF | 50-65<br>% | 51 | NORMOEFFICIENCY |
| INOTROPY<br>ACCELERATION INDEX : ACI | 0.7-1.5 sec-2 | 0.9 | NORMOINOTROPY |
| CHRONOTROPY<br>Heart Rate and/or % Max.Heart Rate | 37-43<br>% of Max.HR | 35 | HYPOCHRONOTROPY |
| PRELOAD = VOLEMIA<br>End Diastolic Index : EDI | 60-110<br>ml/min/m2 | 89 | NORMOVOLEMIA |
| MYOCARD.O2 CONSUMP.<br>Left Cardiac Work Index : LCWI | 3.3-5.3<br>kg/m.m2 | 3.5 | NORMOCAPACITY |
| TOTAL O2 DELIVERY<br>Oxygen Delivery Index : O2DI | 570-795<br>ml/min/m2 | 604 | NORMO-O2-DELIVERY |

FIG. 23B

| Name: D., L. | Height in": 68.5 | #: 2436 |
|---|---|---|
| DoB: 03/30/44 | Weight lbs.: 162.0 | Marital S: M |
| Age: 44.7 | % Over/under: -2.0 | Race: Caucasian |
| Sex: M | BMI: 24 | Date: 12/02/88 |

HEMODYNAMIC ANALYSIS of EXERCISE PERFORMANCE (Ideal Values are calculated at the corresponding Actual Heart Rate)

| PARAMETERS | STANDING | | FIRST EXERCISE LEVEL | | SECOND EXERCISE LEVEL | |
|---|---|---|---|---|---|---|
| | Ideal | Actual | Ideal | Actual | Ideal | Actual |
| | % Diff. of Ideal | | % Diff. of Ideal | | % Diff. of Ideal | |
| TENSION | 95 | 90 | 95 | 108 | 95 | 110 |
| Mean Arterial BP · mmHg | -5.9 | | 13.0 | | 15.8 | |
| GLOBAL BLOOD FLOW | 6.621 | 5.473 | 17.991 | 15.552 | 26.030 2.8 | 26.761 |
| CARDIAC OUTPUT · L/min | -17.3 | | -13.6 | | 3.93 Increasedx4.89 | |
| DYNAMIA | 3.524 | 2.913 | 9.576 | 8.278 | 13.855 | 14.244 |
| Cardiac Index L/min/m2 | -8.4 | | -13.6 | | 2.8 | |
| VOLEMIA | 97 | 89 | 157 | 146 | 182 | 184 |
| PRELOAD ml/min/m2 End Diastolic Volume Index | -8.4 | | -7.0 | | 1.4 | |
| EJECTION | 55 | 46 | 92 | 80 | 109 | 112 |
| Stroke Index ml/min/m2 | -17.3 | | -13.6 | | 2.8 | |
| EFFICIENCY | 56.5 | 51.0 | 58.7 | 54.6 | 60.0 | 60.9 |
| Ejection Fraction % | -9.8 | | -7.0 | | 1.4 | |
| INOTROPY | 1.0 | 0.9 | 2.0 | 1.9 | 2.7 | 2.7 |
| Acceleration Index sec-2 | -9.8 | | -7.0 | | 1.4 | |
| CHRONOTROPY | 35 | 35 | 57 | 57 | 70 | 70 |
| % of Maximum Heart Rate | 0.0 | | 0.0 | | 1.4 | |
| RESISTANCE | 2163 | 2462 | 796 | 1041 | 550 | 620 |
| SVRI dyn.sec/cm5/m2 | 13.8 | | 30.7 | | 12.6 | |
| CAPACITY | 4.5 | 3.5 | 12.3 | 12.1 | 17.8 | 21.4 |
| LCWI kg.m/m2 | -22.5 | | -1.6 | | 20.1 | |

FIG. 23C

NONINVASIVE HEMODYNAMIC ANALYZER ALTERABLE TO A CONTINUOUS INVASIVE HEMODYNAMIC MONITOR

This application is a continuation of U.S. patent application Ser. No. 08/314,732 filed Oct. 3, 1994 now abandoned, which is a continuation-in-part Ser. No. of U.S. patent application Ser. No. 08/140,453 filed Oct. 25, 1993, now U.S. Pat. No. 5,584,298.

BACKGROUND

1. Field of the Invention

This invention relates to a new noninvasive method for calculating Actual Stroke Volume and Cardiac Output of a human heart using computerized algorithms, and to a continuous noninvasive hemodynamic analyzer which computes a complete real-time Hemodynamic Profile in rest and exercise.

2. Description of Prior Art

The principal role of Cardiac Output in the Hemodynamic Hierarchy has resulted in a long felt need for an accurate measurement of blood flow. The fact is that if Cardiac Output is known, a whole sequence of cardiovascular parameters can be calculated with the values of the easily obtainable Blood Pressure Data. A noninvasive, continuous/frequently reapplicable, patient-, and user-friendly, inexpensive method could revolutionize modern health care by treating patients better at less expense.

There are about eight useful methods at the present time for measuring Cardiac Output. The first three are the Fick Method, the Dye-Indicator Dilution Method, and the Thermodilution Method. Three other methods allow visualization of the heart chambers; these include cine-angiography, gated-pool radionuclides, and echocardiography. The two most practical noninvasive methods at the present time are Doppler Ultrasound and Electrical Bioimpedance.

Although all these methods have some merit, there is no absolutely accurate method which could provide a standard to measure Cardiac Output. It is generally accepted in hemodynamic literature that all methods have an inherent inaccuracy of ±10% and their absolute accuracy at best is ±15–20%. Therefore, if any two methods are compared to each other, at least 75% of the points should fall within a ±20% confidence band to establish good correlation.

A problem in the field of Cardiac Output-Measurement is that none of the methods fulfills all ideal requirements. In the following an attempt is made to summarize the ideal requirements on a 100 point scale. The different categories are arbitrarily assigned the same weight for the sake of comparability.

1. Maximum inherent inaccuracy ±10% and absolute accuracy at best ±20% (10 points).
2. General availability for any kind of patient, considering:
   a) no size and/or weight limitation(s) (2 points)
   b) no age limitation(s) (2 points)
   c) no time limitation (continuous measurability) (2 points)
   d) no place limitation(s) (portability of instrument) (2 points)
   e) simplicity of instrumentation (minimal proprietary item(s)) (2 points)
3. Economical, considering:
   a) price for testing for patient (2 points)
   b) price for instrumentation, e.g., buying price of instrument(s) (2 points)
   c) price for place, e.g., home, ambulatory or hospital, etc. (2 points)
   d) price for time, e.g., duration of test for doctor or technician(s) work (2 points)
   e) price for evaluation, e.g., assessment with graphical capability (2 points)
4. Technical make-up, e.g., complication of procedure on the part of examiner or for the examinee (10 points)
5. No setting requirement, e.g., can be operated any place from field to hospital (10 points)
6. No patient risk from any point of procedure (10 points)
7. Availability in any health condition, e.g., post MI-Stress Testing or Cardiac Bypass-Operation and manageability of testing procedure in any body position, e.g. supine, standing or moving (10 points)
8. Instantaneous repeatability and/or continuous monitoring, e.g., under surgical procedure, postoperative care, etc. (10 points)
9. Real-time recognition of the patient's hemodynamic profile, e.g., instantaneous Computer Programming Capability (10 points)
10. Instantaneous availability and/or directions for therapeutic management (10 points).

Prior art cardiac output measurement methods use direct or indirect algorithms to make the displayed value as close to the actual cardiac output as possible.

The current clinical standard for invasive measurement of Cardiac Output, for example, implements the Stewart-Hamilton equation. A thermodilution computer calculates the different correction algorithms. Its inaccuracy, which can be ±20% from the actual cardiac output, is clinically acceptable and this method is used in spite of risk associated with this invasive method, its high cost, its intermittent capability of use and its other major inherent inconvenience, the possibility of infection.

A need exists, therefore, for the continuing development of noninvasive methodologies to measure cardiac output. Presently only two types of noninvasive methods are available for continuous application: the Doppler ultrasonography and electrical bioimpedance methods.

The theoretical basis for the Doppler ultrasonography (continuous wave) method is the Doppler effect. Sound waves undergo a frequency shift when the distance between the generator and the receiver is changing. Doppler ultrasonography (Ultracom) is a reliable noninvasive procedure for one clinical setting and its accuracy is directly proportional to several technical assumptions. At best, the absolute accuracy of present continuous-wave Doppler ultrasonography systems is no better than ±45% of the actual cardiac output. The frequency of use is very limited and the systems are hospital-based. Furthermore, the results obtained by this method are user-dependent and the equipment requires a skilled operator.

The theoretical basis of the electrical bioimpedance method is the fact that the electrical conductivity of the thorax is proportional to the thoracic fluid content. Its changes are the result of volumetric and velocity variation of blood (the most electrically conductive substance in the body) in thoracic vessels. These measured variables, together with the volume of intrathoracic tissue (estimated by different algorithms of the computer from height, weight, and sex of the patient), are the basis for calculation of Stroke Volume and Cardiac Output.

BoMed Medical Manufacturing, Ltd., Irvine, Calif. markets its NCCOM3 instrument which uses an electrical bioimpedance methodology. BoMed's NCCOM3 has its clinically verified algorithms for cardiac output measurements within ±20% of the actual value in the majority of monitored patients. Compared to other methods, such as Doppler ultrasonography, this method has advantages; more user-friendliness, unlimited applicability and repeatability, increased accuracy and above all, it provides an estimate of volemic status and oxygen delivery.

However, these heretofore known methods have major shortcomings. With regard to continuous-wave Doppler ultrasonography, the maximum inherent inaccuracy and/or the absolute accuracy is not appropriate; the system is not patient or user-friendly, it is not a hands-off technique, there is inadequate accuracy at different flow levels, usability is limited (e.g. requires sterile environment) and it is not economical.

With regard to electrical bioimpedance measurements, there are the following shortcomings: Limited in-patient and user-friendly aspects; complicated technical make-up, e.g., physician's understanding of algorithms and their limitations; limited availability of the instrument (hospital setting); limited usability in some health conditions, concerning electrode-placements (proprietary items); inseparability of patient and instrument, e.g., the data obtained is inherently tied to the function of the instrument and one cannot use literature sources to reproduce previous evaluations; and lack of economy.

The present invention overcomes the problems which currently exist in the field of Cardiac Output measurement methods and is able to approach the ideal requirements noted above, up to about 94%, in contrast with the Doppler and bioimpedance techniques, which meet only about 50–70% of the ideal requirements. In particular, these methods are not able to meet the following requirements:

1. Simplicity of instrumentation and/or no proprietary item(s)
2. Economy—price of each instrument is prohibitively high, therefore, patient's expenses are increased
3. Technical make-up—complication of procedure
4. Setting-requirement—mostly hospital setting
5. Maneuverability of testing procedure.

SUMMARY OF THE INVENTION

Accordingly, a primary object of the invention is to provide a noninvasive cardiac output analyzer which uses a new method and apparatus unknown in the prior art.

A further object of the invention is to provide a cardiac output analyzer which is based on a network of algorithms, but which uses generally available blood pressure (systolic and diastolic) and heart rate data, as well as height, weight, and sex of the patient, date of birth, and the present date. The only nonobligatory data is the Hemoglobin level, but without it the algorithm calculates the Oxygen Delivery Index with the average Hemoglobin value according to the sex of the patient.

A further object of the present invention is to provide an economical approach to cardiac output measurement that provides reliable accuracy unknown in the prior art.

Yet another object of the present invention is to provide a novel patient and user-friendly device capable of real-time measurement of the patient's hemodynamic profile in rest and exercise modes.

Still another object of the present invention is to provide a means for evaluating and/or screening a large number of people for cardiovascular conditions noninvasively in an ambulatory setting, e.g., for sports medicine, military recruitment, or commercial pilot testing.

A further object of the invention is to provide a novel unlimited continuous digital and/or graphical display of a comprehensive cardiodynamic profile for intensive care units, cardiac, surgical and postoperative units using an arterial line for continuously and invasively obtaining systolic & diastolic blood pressure and heart rate readings.

An additional object of the invention is to provide a device which, used simultaneously with electrocardiography, will significantly increase the specificity and sensitivity of a treadmill stress test.

Another object of the invention is to provide a method and apparatus for collecting hemodynamic data in any type of exercise without any restriction, which can be used conveniently for exercise testing of a large number of people who cannot afford the conventional treadmill exercise test.

Still another object of the present invention is to provide an investigative method useful in the presence of stressful conditions which could affect the patient's cardiovascular system. In this case the present invention provides a very convenient method to investigate certain psychosomatic stress-effects (such as hyperventilation, cold pressure, positional changes, etc.) on the patient's real-time hemodynamic constellation and by this technique a new and scientifically based method of stress management can be obtained. This approach will be very valuable to check a larger number of patients in actual work-settings, e.g. occupational medicine, military, commercial pilots, and testing.

A further object of the present invention is to provide an educational device for medical students and other health workers. With the help of the computer many hemodynamic constellations and/or individual changes can be studied, presented or reconstructed in a manner which is helpful for prognostic and/or therapeutic viewpoints of certain cardiovascular conditions.

The present invention provides a method for hemodynamic analysis and an automatic computerized hemodynamic analyzer which produces a variety of useful diagnostic displays and calculations. The method is used to calculate Actual Stroke Volume and Cardiac Output of a human heart, and is implemented in a continuous noninvasive hemodynamic analyzer which computes a complete real-time Hemodynamic Profile with twelve parameters, in both rest and exercise modes. Inputs are received noninvasively by the analyzer, and a cascade of algorithms are used to calculate Stroke Volume, Ejection Fraction and Acceleration Index in rest and exercise modes. The analyzer displays or prints a summary in graphical form.

In accordance with the present invention it is possible to diagnose and treat Hypertensive Disease on a hemodynamic basis, etiologically and not symptomatologically. The method and apparatus of the invention makes it possible to perform these tasks economically and without restriction, e.g., expenses, place, mobility, technical make-up, etc. Large numbers of patients can be evaluated in a relatively short time and with the graphical-printout capability provided by the invention, patient follow-up is easy and comprehensible.

The method may also decrease the use of the invasive Swan-Ganz catheter, which is associated with several important potential complications. The Noninvasive Hemodynamic Analyzer is able to obtain data directly and continuously about the preload: Left Ventricular End Diastolic Volume, which is closely related to the Pulmonary "Wedge" Pressure.

The Noninvasive Hemodynamic Analyzer calculates $VO_2$: Maximal Oxygen Consumption and its derivatives: METs level during exercise. This method measures these parameters directly from the Cardiac Output and computes for graphical representation the Exercise Capacity in Percentage (Efficiency Ratio).

The primary advantage of the present invention over the prior art is the simplicity of the method, which is also (as in the case of other noninvasive approaches, namely Doppler and electrical bioimpedance) based on a network of algorithms—but using generally available systolic and diastolic blood pressure and heart rate data. The other obligatory inputs are easily obtainable (height, weight, sex, date of birth, and the present date). The only non-obligatory data is the hemoglobin level, but if this is not available the algorithm calculates the oxygen delivery index with the average hemoglobin value according to the sex of the patient.

Another primary feature that differentiates the present invention from previous noninvasive methods and devices is its mobility and maneuverability. It has no setting requirement(s). It can be used in any situation, position, or place, sterile or non-sterile.

A further feature that makes present invention very convenient is its economy. The price of the testing device (and thus the test) is significantly less than the cost of the prior art devices.

Still another primary feature that differentiates the invention from the prior art is the generous graphical presentation produced by the system, which covers every aspect of any hemodynamic changes and makes the evaluation and/or follow-up of either ambulatory and/or surgical patients very comprehensible on the computer screen and/or in printed form, at the nursing station, during anesthesia & surgery, etc.

Further objects and advantages of my invention will become apparent to those skilled in the art from consideration of the following description with reference given to the appended drawings.

BRIEF DESCRIPTION OF THE DRAWINGS

FIG. 4 gives information about the composition of the Cardiac Index. For example, if the Stroke Index is increased but a normal Cardiac Index exists, the seemingly normal Cardiac Index is the result of the compensatory product of the increased Heart Rate.

FIG. 7 is a diagnostic graph produced by the present invention showing Hemodynamic Reactivities for position changes from supine to upright. Cold pressure test and hyperventilation are represented by the groups of changes (changes are expressed in percentage of the average normal values) such as:

1. Mean Arterial Pressure, Stroke Index, Heart Rate, and Systemic Vascular Resistance; and
2. End Diastolic Index as Preload, Cardiac Index & Acceleration Index as Myocardial Contractility and Systemic Vascular Resistance as Afterload.

Figure 7:
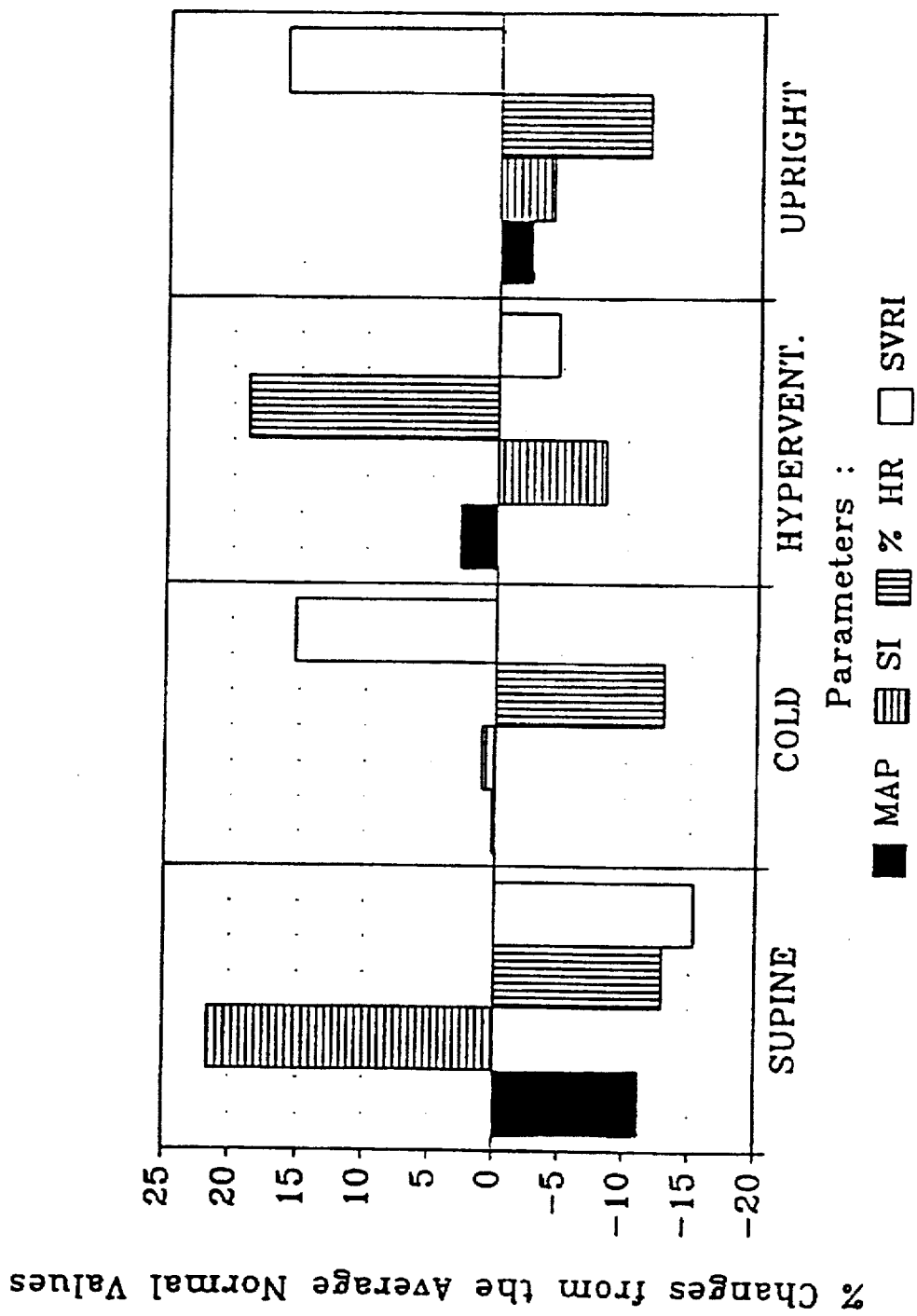
Figure 8:
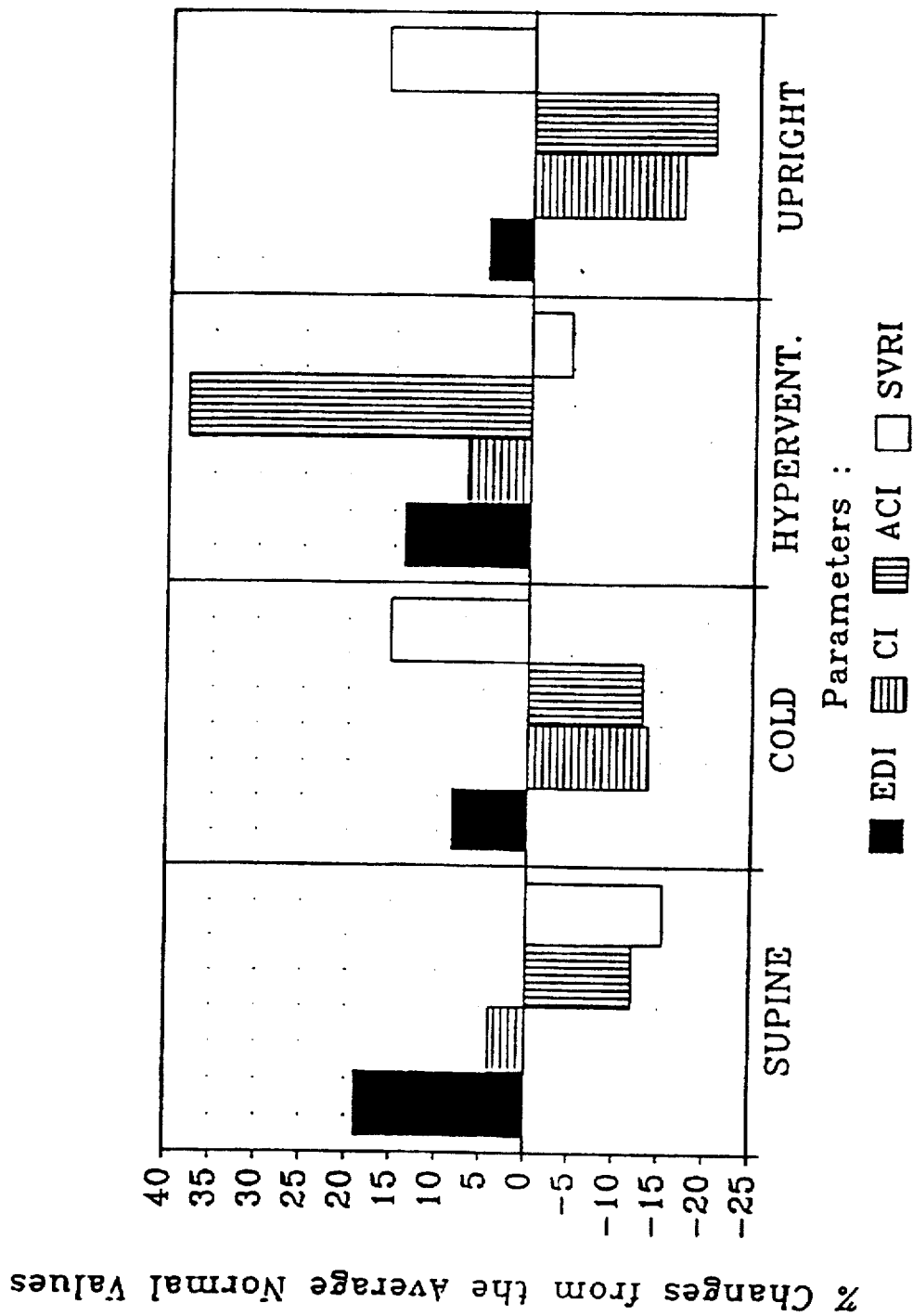

FIG. 8 is a diagnostic graph produced by the present invention, similar to FIG. 7, showing hemodynamic reactivities during psychosomatic stress stimuli for Preload (EDI), Myocardial Contractility (CI & ACI) and Afterload (SVRI).

Figure 9:
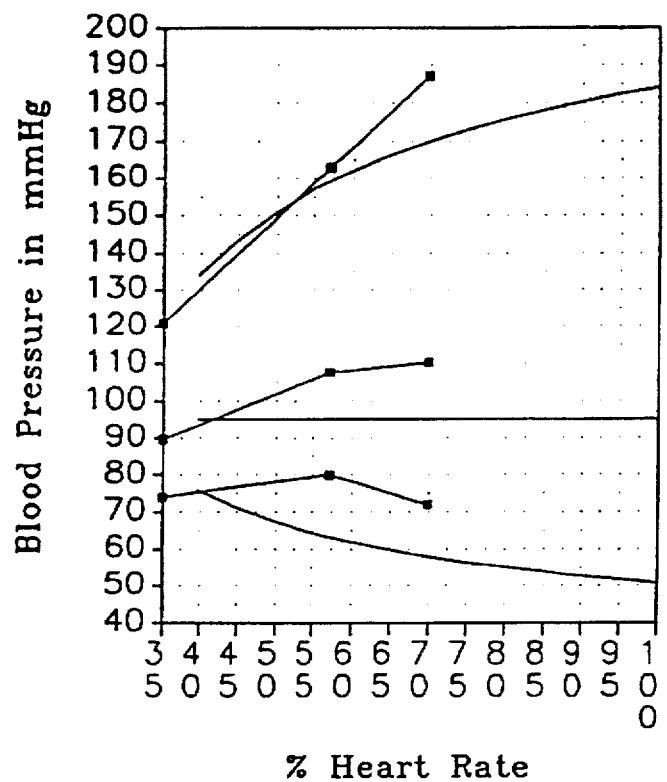

FIG. 9 is a diagnostic graph produced by the present invention, showing actual and ideal blood pressure values (Systolic, -Diastolic-, and Mean Arterial Pressure) plotted against the % Heart Rate. By this graphic representation the trend of exercise responses can be easily demonstrated by comparison to the Ideal Values of these parameters.

Figure 10:
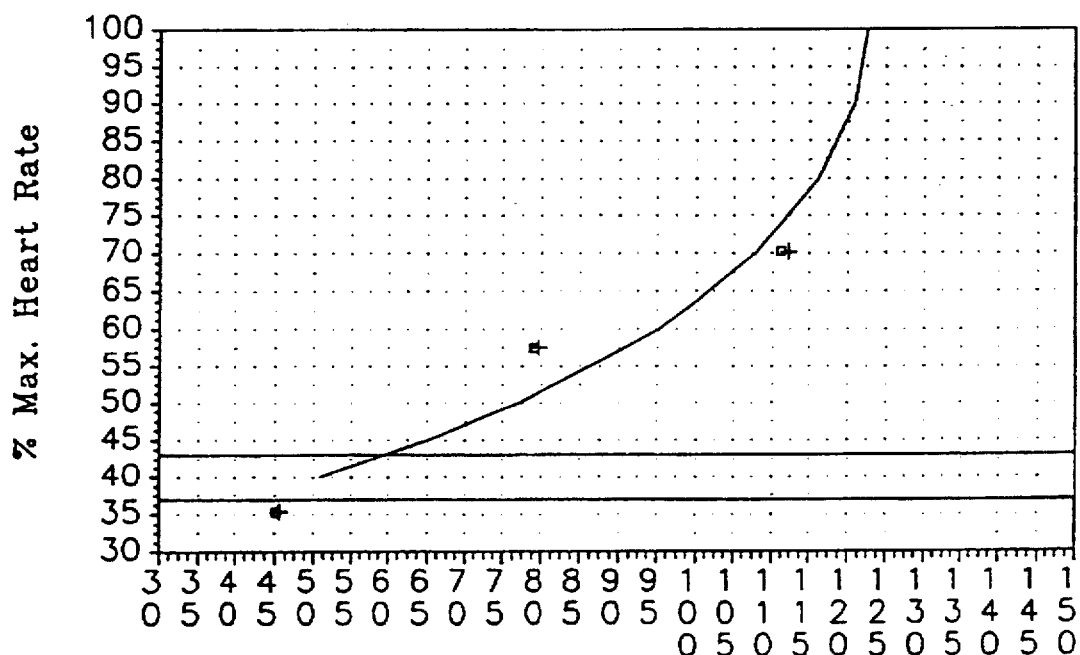

FIG. 10 is a diagnostic graph produced by the present invention, showing stroke index changes plotted against % Heart Rate changes during an exercise test. The normal testing % Heart Rate range and the Calculated Ideal Stroke Index Values (with the Ideal Body Surface Area) are indicated. Actual Stroke Indices are represented with Actual Body Surface Area and with Ideal Body Surface Area. Information obtained this way shows the exercise indicated Stroke Index changes in comparison to the Heart Rate, as influenced by the Body Size and Blood Pressure changes, to indicate the functional capacity of the left ventricle.

Figure 11:
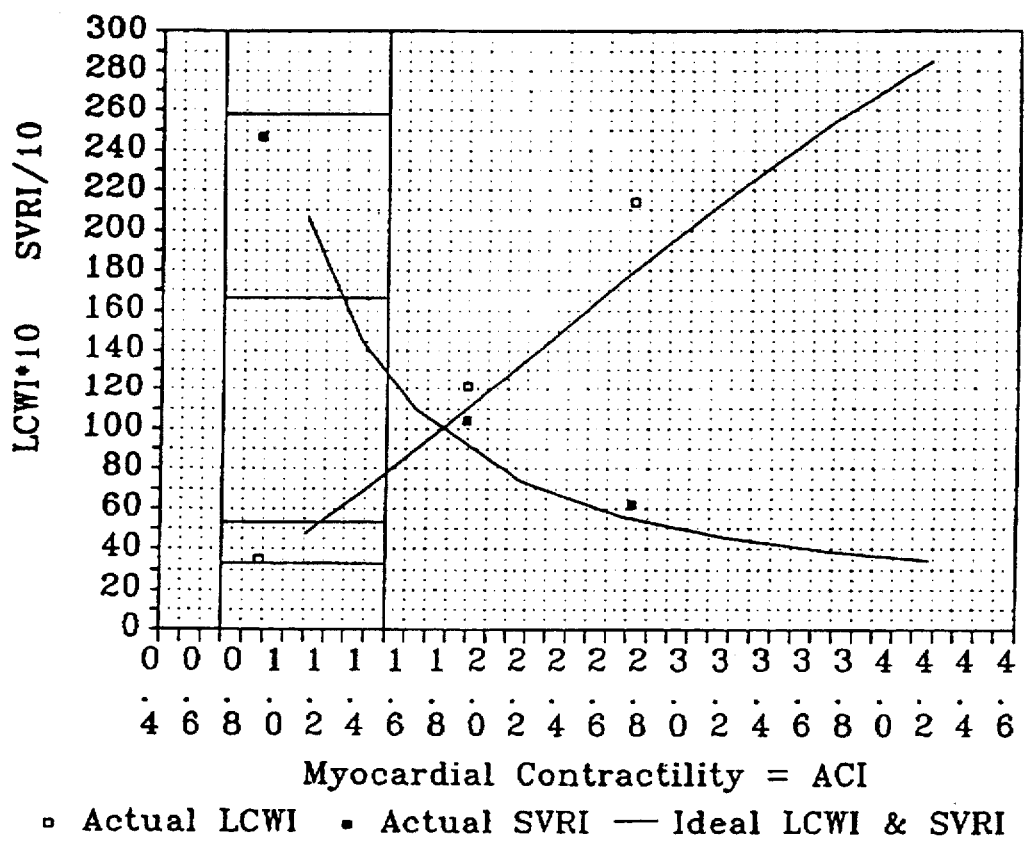

FIG. 11 is a composite graph showing hemodynamic changes during Exercise, which presents interactions among preload (as end diastolic index), myocardial oxygen consumption (as Left Cardiac Work Index), and afterload (as systemic vascular resistance index). For comparison the Ideal Indices of these parameters are also provided.

Figure 12:
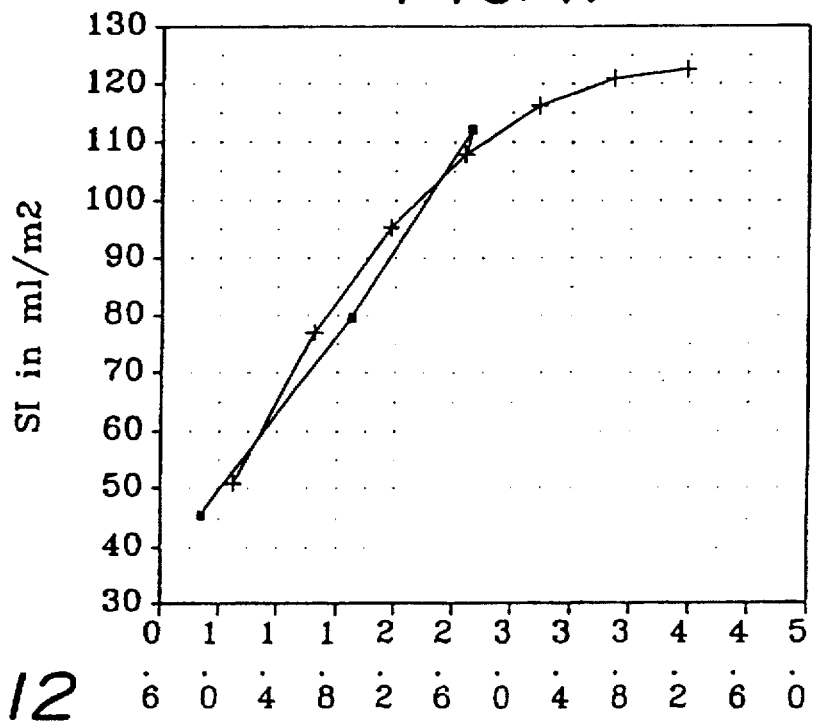

FIG. 12 is a graph produced by the present invention depicting a Starling Law curve, represented by plotting stroke index (SI) values against myocardial contractility (Acceleration Index) changes during an exercise test. The normal heart exhibits an ascending curve, for the major portion of the myocardial contractility changes. However, a failing heart may produce a flattening or descending curve direction.

Figure 13:
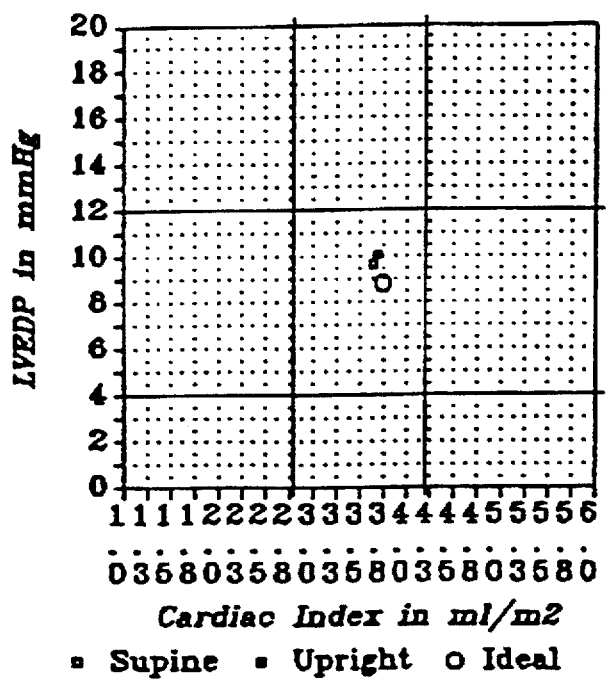

FIG. 13 is a graph produced by the present invention showing left ventricular end diastolic pressure in relation to cardiac index at rest. Left ventricular end diastolic pressure (pulmonary "wedge" pressure) is plotted against the Cardiac Index. By this presentation it is immediately possible to obtain the state of pulmonary volemia and the peripheral perfusion with hypo-iso-and-hyper-designation of each projected point in Supine and Upright positions.

Figure 14:
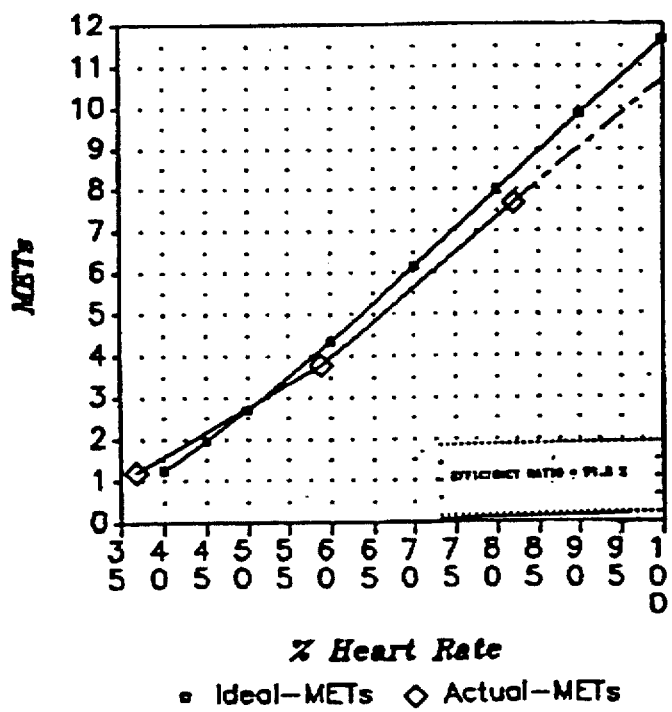

FIG. 14 is a graph produced by the present invention showing oxygen consumption by plotting MET against % Heart Rate changes during exercise. The graph shows the actual METs in correlation to the ideal METs, and the resultant Efficiency Ratio in %.

Figure 15:
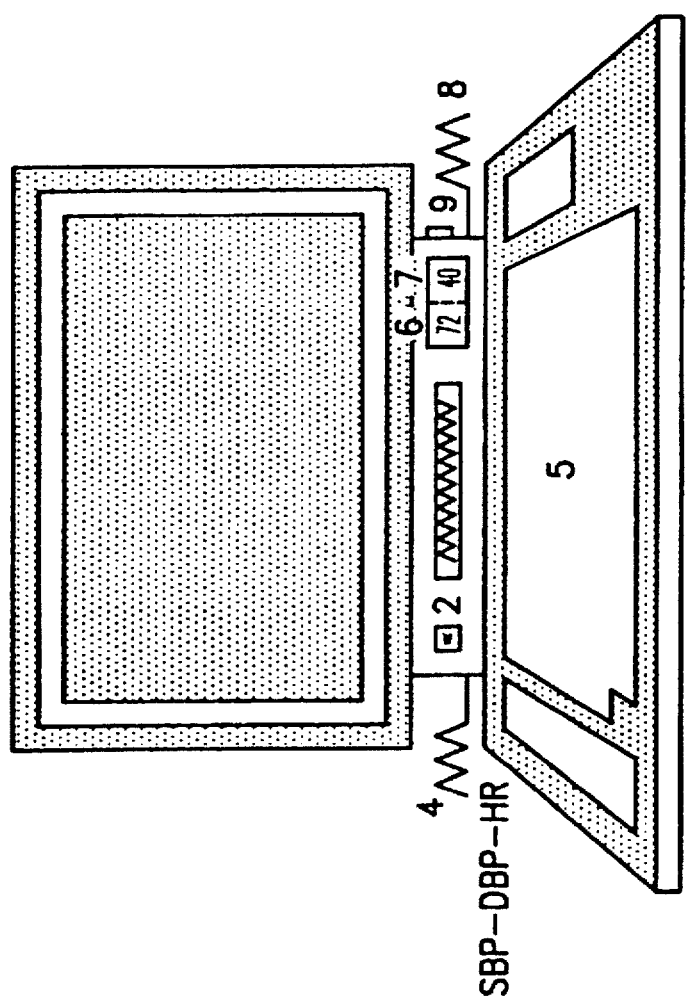

FIG. 15 is a drawing showing the hemodynamic analyzer apparatus of the present invention.

Figure 16:
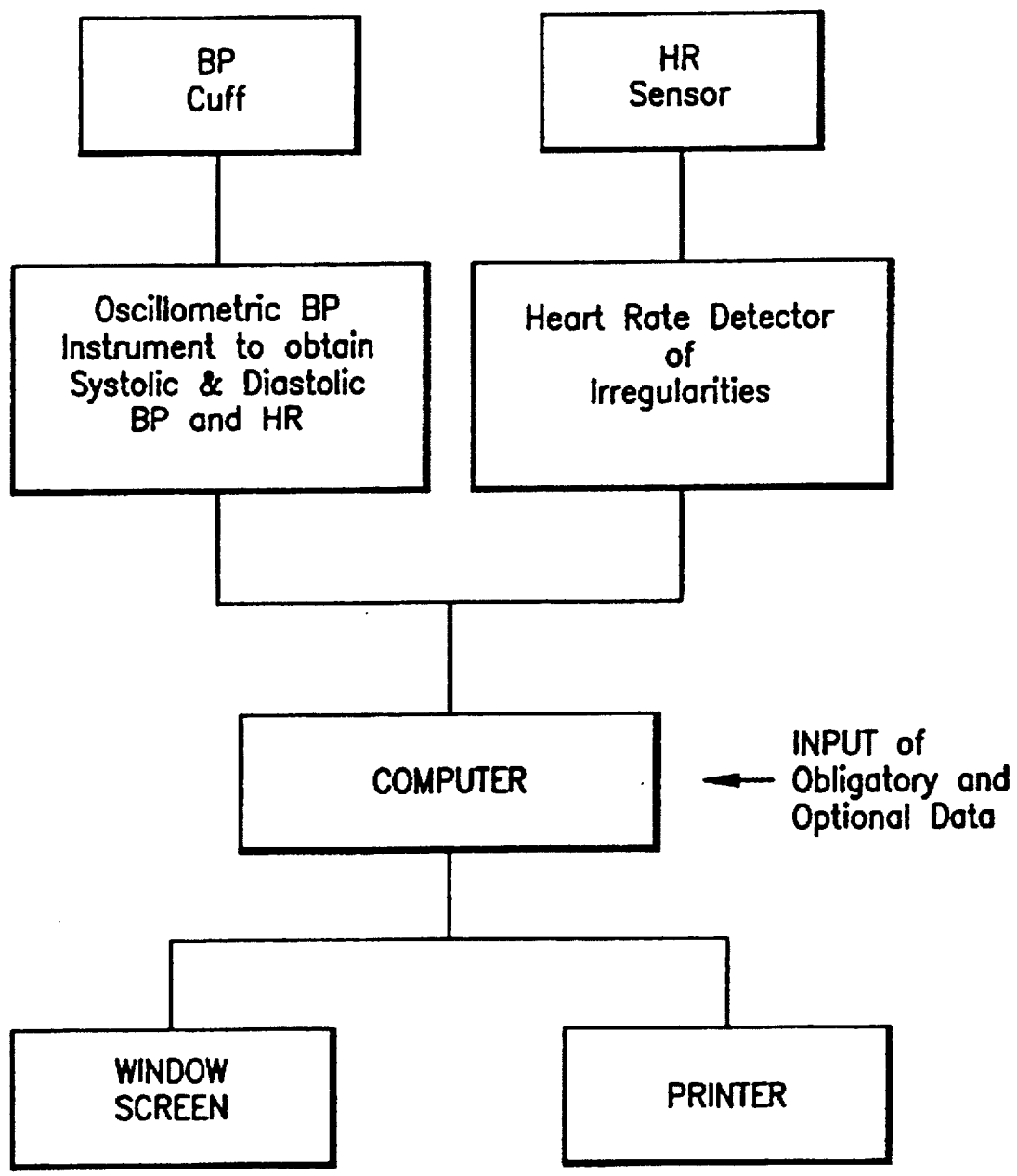

FIG. 16 is a block schematic diagram of the hemodynamic analyzer apparatus of the present invention.

FIG. 17 is a schematic diagram of the operational procedures used by the present invention, showing the transition from inputs to intermediary parameters to final parameters.

FIG. 18 is a digram showing the hemodynamic interactions of the main cardiovascular parameters produced by the present invention.

Figure 19A:
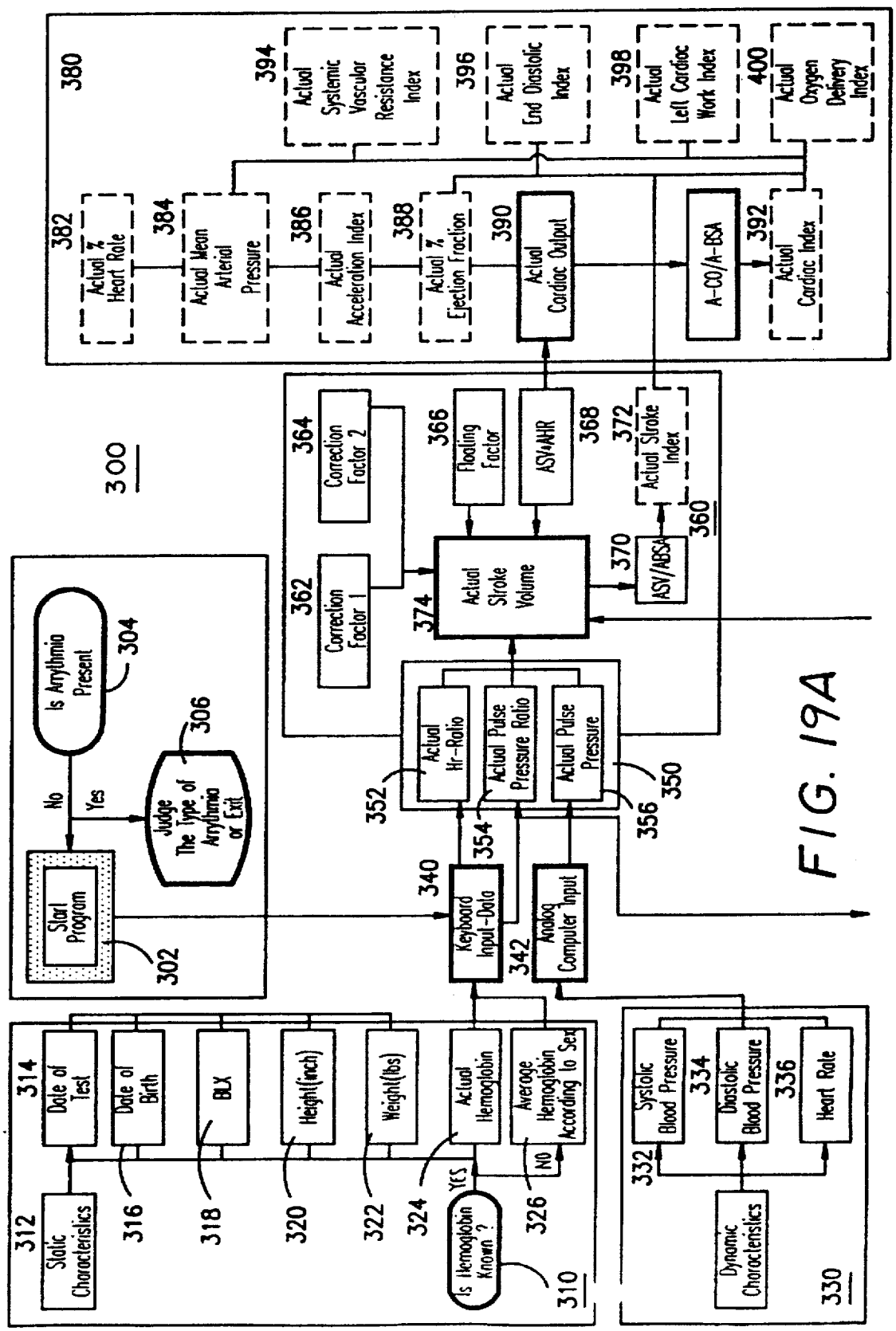
Figure 19B:
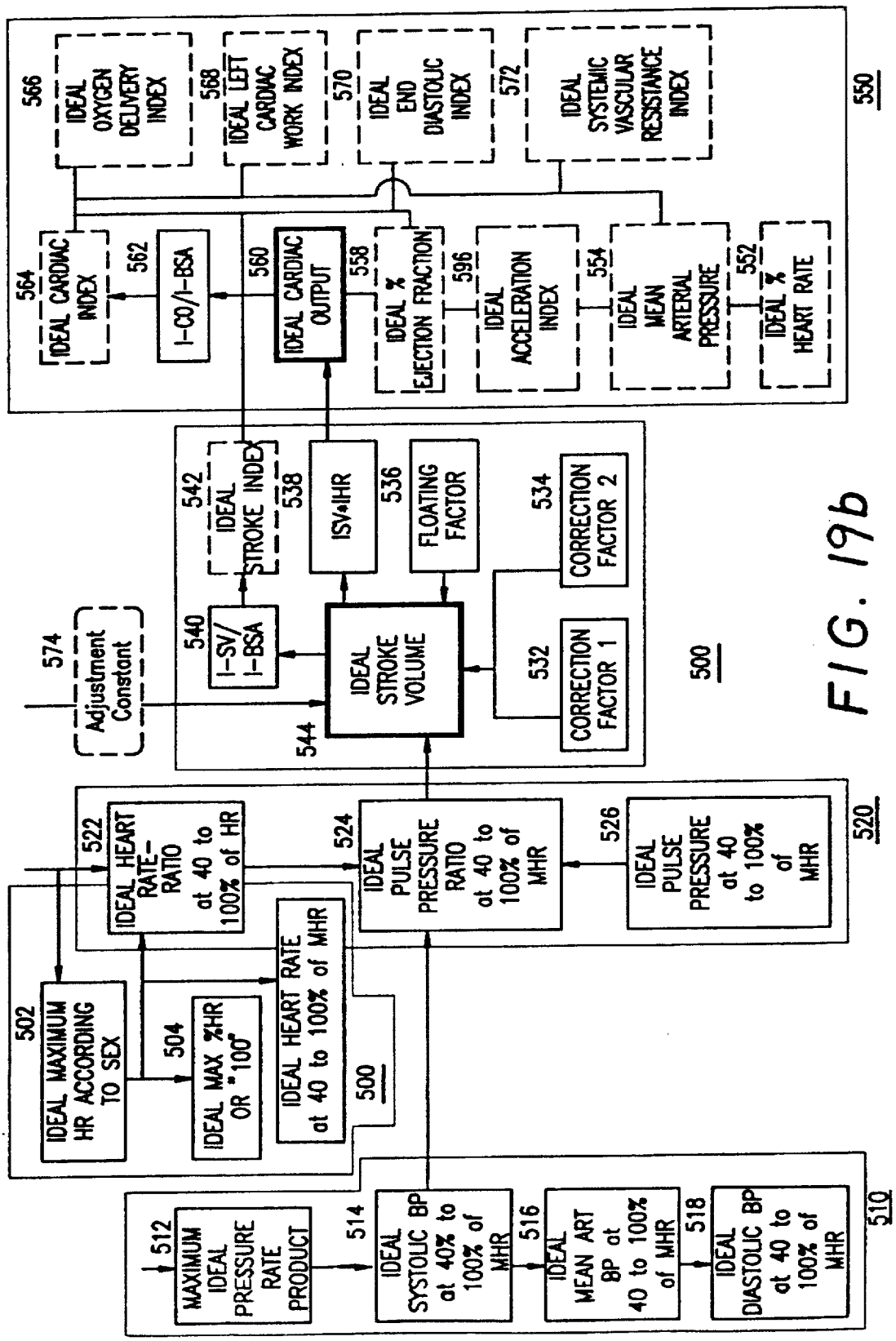

FIGS. 19a and 19b together constitute a flowchart of an algorithm for computing actual and ideal hemodynamic parameters according to the present invention.

FIG. 20 is a flowchart showing the operation of the present invention to computing hemodynamic profiles.

Figure 21:
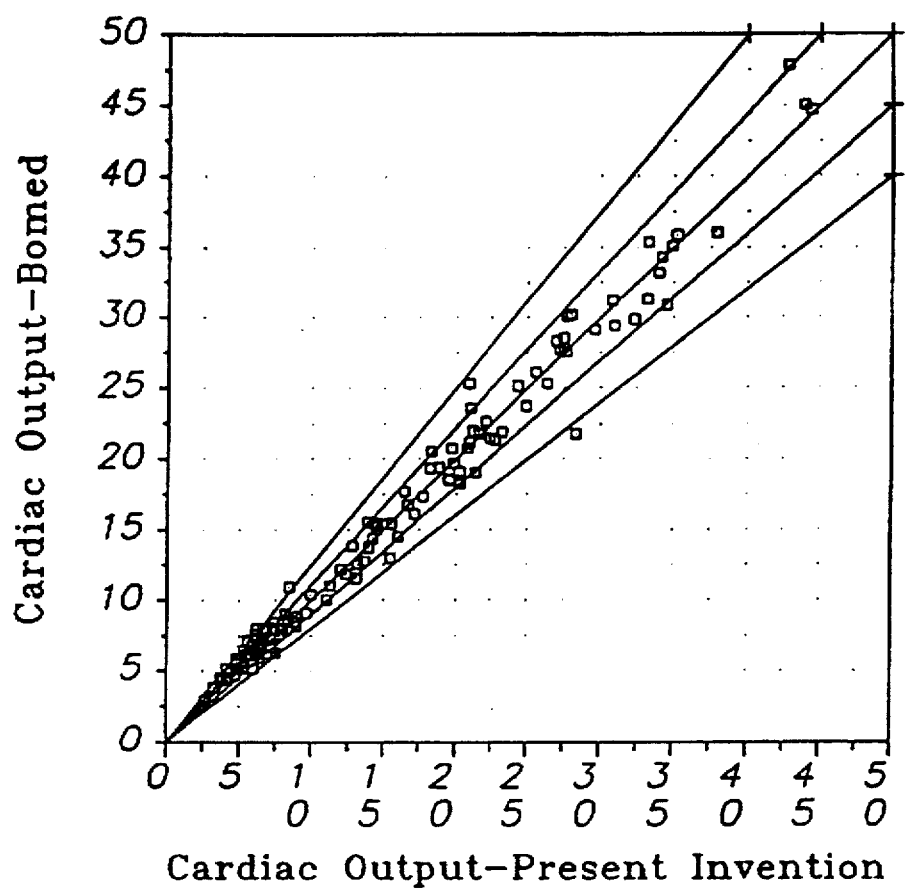

FIG. 21 is a scattergram providing a statistical comparison of the output of the present invention with the output of a Bomed electrical bioimpedance measurement device.

FIG. 22 is a table showing a statistical summary of the scattergram of FIG. 21.

FIGS. 23a and 23b show the data collected for a sample patient in the resting (supine and upright) positions. FIG. 23c shows data collected for the sample patient during the exercise stress test.

DETAILED DESCRIPTION OF PREFERRED EMBODIMENTS

The present invention provides a method for hemodynamic analysis and an automatic computerized hemodynamic analyzer which produces a variety of useful diagnostic displays and calculations.

First, the method of performing the calculations according to the present invention will be described in detail.

The invention applies two calculation cascades to obtain the actual stroke volume and the corresponding hemodynamic state of a particular adult patient.

Through the first step the ideal stroke volume and the corresponding ideal hemodynamic pattern are calculated. In the second sleep the actual stroke volume is computed by a factor (adjustment constant) relative to the corresponding ideal stroke volume.

To calculate the ideal stroke volume of a particular patient the following physiological correlation is utilized:

a) The pressure rate product (systolic BP * HR/100) plotted against HR is a linear correlation.

b) The maximal average heart rate can be obtained by using Regression Coefficients according to age and sex.

c) Normal heart rate in a resting state is assumed to be 40±3% of the calculated maximal heart rate.

d) From the maximal ideal pressure rate product (sex dependent) the ideal systolic blood pressure values can be calculated for any given heart rate:

$$PRP = \frac{SBP*HR}{100} \rightarrow SBP = \frac{PRP*100}{HR}$$

e) Considering that mean arterial blood pressure is the geometric average of the pulse area between SBP and DBP (an approximate triangle): $MAP-[(SBP-DBP)/3]+DBP$. Therefore, f) $DBP=MAP-[(SBP-MAP)/2]$ g) Thus through steps a) through f) an ideal systolic and diastolic blood pressure curve can be computed according to the corresponding heart rate, as ideal dynamic parameters.

h) With the above obtained dynamic parameters and static parameters, such as patient's age, height, weight (ideal weight for height and frame), sex and hemoglobin content—an ideal stroke volume and the corresponding ideal hemodynamic profile can be calculated by the series of equations given herein.

The calculation of stroke volume is based on a theoretical model of pulse wave propagation. In the aorta and/or blood vessels the manifestation of systolic blood pressure as a pulse wave originates by the constriction of the left ventricle (systole). Although the values are different at the aortic level, the resulting mean arterial pressure is practically the same at the cubital area where blood pressure is measured.

The true stroke volume (or cardiac output) can be measured only in the ascending aorta. However, that part of the blood volume which creates the pulse wave in the peripheral major vessels is synchronous in time (pulse rate) with the bolus of the stroke volume. The pulse wave is the result of the oscillation of systolic and diastolic pressure and their difference at the largest expansion is equal to pulse pressure. Calculating the average pulse pressure ratio as (systolic blood pressure–diastolic blood pressure) /(60/HR), we can take this result empirically as the largest circumferential extension of the blood vessel.

If we assume that the pulse pressure ratio (PP–R) is essentially the circumferential change of pulse wave→2 $r*\Pi$, we can calculate the area, equal to $r^2*\Pi$, therefore $$r = \frac{PP-R}{2*\Pi} \rightarrow \left|\frac{PP-R}{2*\Pi}\right|^2 *\Pi \qquad \text{Eq. 1}$$

The goal in this case is to calculate the Pulse Wave Volume, so the approximate propagated bolus size (blood volume increase) will be equal to $$\left|\frac{PP-R}{2*\Pi}\right|^2 *\Pi/(60/\text{HeartRate}). \qquad \text{Eq. 2}$$

Multiplying the above equation by a floating factor and taking the square root value, a so called ideal stroke volume is empirically calculated, as divided by the basal surface area→ideal stroke index. This assumption is based on an adjustment of systolic-diastolic and heart-rate values to the sex, weight, and age of individual patient (Ideal BP & HR values). The actual stroke index is calculated in the same way but it is corrected by an adjustment constant, obtained as the difference between the Ideal Preliminary and Adjusted cardiac indices.

More specifically, these ideal parameters are calculated as follows. Pulse Wave Volume is determined based on the Ideal Pulse Pressure Ratio I-PP-R according to Equation 2 above. The Preliminary Ideal Stroke Volume (I-SV$_P$) is then calculated using equation 3a below, but without multiplying by adjustment constant L. The Preliminary Ideal Stroke Volume is converted to a value of Preliminary Ideal Cardiac Output (I-CO$_P$) by multiplication with the Ideal Minimum Heart Rate (designated as 40% of the Ideal Maximum Heart Rate). The Preliminary Ideal Cardiac Output is then indexed by dividing by an Ideal Body Surface Area (I-BSA) to obtain a Preliminary Ideal Cardiac Index (I-CI$_P$). I-CIp is then adjusted according to age using the formula ((70-age)

\*0.35/50))+3.5 to obtain the real Ideal Cardiac Index (I-CI). The difference between I-CI$_p$ and I-CI is then used as an adjustment constant in calculating an actual cardiac index, actual cardiac output, actual stroke volume, and actual stroke index, in a manner which will be explained in more detail below.

The present invention provides algorithms to calculate the following parameters:
1. STROKE VOLUME (Eq. 3)
2. ACCELERATION INDEX (Eq. 4)
3. % EJECTION FRACTION (Eq. 5)
4. IDEAL PRESSURE RATE PRODUCT (Eq. 6)
5. IDEAL SYSTOLIC PRESSURE (Eq. 7)
6. IDEAL DIASTOLIC PRESSURE (Eq. 8)
7. IDEAL PULSE PRESSURE (Eq. 9)
8. IDEAL PULSE PRESSURE RATIO (Eq. 10)
9. IDEAL MAP (Eq. 11)
10. IDEAL LVEDP (Eq. 12)
11. IDEAL VO$_2$/METs (Eq. 13)

These algorithms will now be disclosed in more detail, starting with the algorithm used to calculate the stroke volume.

CALCULATION OF STROKE VOLUME

1. If Heart Rate is >or=40% of Maximum Heart Rate:

$$SV = \sqrt{\Pi * B * C * L} * \frac{A}{\Pi * 2} * \frac{D}{1000} \qquad \text{Eq. 3a}$$

A=PULSE PRESSURE RATIO-Actual: Pulse Pressure-Actual/(60/Heart Rate-Actual)
B=Heart Rate Ratio-Actual in [msec]=60/Heart Rate-Actual
C=Floating Factor=((100-% Heart Rate-Actual)*E)+F
D=Heart Rate-Actual
E=Correction Factor 1=(1/K-1/G)/60
F=Correction Factor 2=1/G $G$ = PulsePressure − IdealMaximum*$HR$ − $IM$*

$$\sqrt{(HR - IM/15 * \Pi)} \quad /1400*BSA - I*H$$

where BSA-I is the ideal body surface area in m$^2$.
H=If Age<=70 then ((70−Age)*I)+J else
  If Age>70 then J
I=If Sex=M then 0.08
  If Sex=F then 0.07
J=If Sex=M then 4
  If Sex=F then 3.5

$K$ = PulsePressure − IdealMaximum*HeartRate − $IM$*

$$\sqrt{(HeartRate - IdealMaximum/15*3.14)} \quad /1400*BSA - Ideal$$

L=Adjustment Constant=Preliminary CI-Ideal−Adjusted CI-Ideal
2. If Heart Rate is <40% of Maximum Heart Rate:

(Eq. 1/Heart Rate-Actual)*(Heart Rate-Ideal Maximum−Heart Rate-Actual)+Eq. 1 (Eq. 3b)

CALCULATION OF ACCELERATION INDEX (ACI)

The acceleration index (ACI) expresses the initial speed of ejected blood from the left ventricle in the first 20 milliseconds before the state of peripheral vessels can interfere. The ACI parameter closely represents the true myocardial contractility.

$$ACI = \sqrt{PulsePressure - Actual*5.56 \times 10^{-6}} * \qquad \text{(Eq. 4)}$$

$$\text{Coefficient} = \frac{X}{\sqrt{PulsePressure - Ideal*5.56 \times 10^{-6}*HeartRate-}}$$

where X is 1/1 for a male subject and 1/3 for a female subject.

CALCULATION OF EJECTION FRACTION (EF)

In the first step an Ideal EF is calculated and adjusted to Heart Rate:

EF$_{Ideal}$=((% Heart Rate-Actual−40)*0.1)+57%
HR-Actual=HR*100/Max HR
57=Theoretical Average of EF In the second step the Actual EF is calculated:

$$\text{Actual}EF = \sqrt{\frac{PP - A*HR - A}{PP - I*HR - I}} *EF - I \qquad \text{(Eq. 5)}$$

The calculation of the ideal pressure rate product will now be explained in detail.

CALCULATION OF IDEAL PRESSURE RATE PRODUCT (PRP-I)

If Actual %HR<40 then PRP-I=A−((40−Actual% HR)*G)
If Actual %HR>40 then PRP-I=((Actual %HR−40)*G+A)
If Actual %HR=40 then PRP-I=A  (Eq. 6)

where:
A=((B*C)*((D*40)/100))/100)→Minimum Ideal PRP
B=If Age<=20 then B=105
  If Age>50 then B=140 → Minimum Ideal Systolic BP
  Else B=((Age−20)*C)+105
C=(140−105)/30
D=If Sex=M then D=227−(1.032*Age)→Maximum Heart Rate
  If Sex=F then D=206−(0.597*Age)
E=(D*40)/100→Minimum Heart Rate at 40% of Maximum Heart Rate
F=(100−40)→Maximum Range of Ideal % HR
G=F/60

CALCULATION OF IDEAL SYSTOLIC BLOOD PRESSURE (SBP-I)

SBP-Ideal=(Pressure Rate Product-Ideal*100)/Heart Rate  (Eq. 7)

CALCULATION OF IDEAL DIASTOLIC BLOOD PRESSURE (DBP-I)

DBP-Ideal=Mean Arterial Pressure-Ideal−((Systolic Blood Pressure-Ideal−Mean Arterial Pressure-Ideal)/2  (Eq. 8)

CALCULATION OF IDEAL PULSE PRESSURE (PP-I)

PP-Ideal=Systolic Blood Pressure-Ideal−Diastolic Pressure Ideal both at the same Heart Rate-Ideal  (Eq. 9)

CALCULATION OF IDEAL PULSE PRESSURE RATIO (PP-R-I)

PP-R-I=PP-IDEAL/(60/HR)  (Eq. 10)

CALCULATION OF IDEAL MEAN ARTERIAL PRESSURE (MAP-I)

$$MAP\text{-}I = (Age-20)*0.46 + A \quad (Eq.\ 11)$$

where A=81 for females and 84 for males.

CALCULATION OF IDEAL LEFT VENTRICULAR END DIASTOLIC PRESSURE $$LVEDP = (30.16 * \log 10(\text{End Diastolic Index})) - \log 10(44)) \quad (Eq.\ 12)$$

CALCULATION OF IDEAL OXYGEN CONSUMPTION/METs $$VO_2 = ((((1.5/60)*(60-(100-\%HR))+4)*CO*10)/LBW \quad (Eq.\ 13)$$

METs = $VO_2/3.5$

Using these calculated parameters, it is possible to calculate the whole hemodynamic spectrum with equations available in the hemodynamic literature, in the following manner.

All measured and calculated parameters related to blood flow, such as cardiac output, are body mass dependent and their values cannot be used to assess the adequacy of oxygen transport or pump performance. However, when these parameters are normalized by the patient's Body Surface Area (BSA), the resulting indexed values, such as cardiac index, then become body mass independent. Only indexed parameters should be used for clinical processing of patient data.

BODY SURFACE AREA (BSA) is calculated by the Du Bois formula $$\text{BSA in square meters} = \text{weight}[kg]^{0.425} \times \text{height}[cm]^{0.725} \times 0.007184$$

| | | |
|---|---|---|
| Male: ((235−55)*(Height in inch − 48)/(84−48)) + 55 | | |
| Female: ((225−45)*(Height in inch − 48)/(84−48)) + 45 | | |
| According to Frame: | Small | 90% |
| | Small/Medium | 95% |
| | Medium Ideal BW: | 100% |
| | Medium/Large | 105% |
| | Large | 110% |

LEAN BODY MASS
Male: (IBW in lbs*100/115)/2.2046 [in kg]
Female: (IBW in lbs*100/125)/2.2046 [in kg].

The following parameters are used for hemodynamic analysis in the present invention and the invention provides and uses these algorithms:

1. Stroke Index (SI): SI is the ejected blood volume from the left ventricle during systole and calculated as:

Eqs. 3a and 3b: Stroke Volume/Body Surface Area

Normal Range of Stroke Index (resting-supine adults): 35–65 ml/m²

2. Cardiac Index (CI): Global Blood Flow represented by CI—the most important Oxygen-Transport-related parameter which is the indexed Cardiac Output [L/min/m²].

CI=CO/BSA where CO is Cardiac Output in L/min.

Normal Range of Cardiac Index (resting-supine adults): 2.8–4.2 l/min/m²

3. AFTERLOAD: Systemic Vascular Resistance Index (SVRI) [dyn.sec.cm$^{-5}$m²]

The ratio of Mean Arterial Blood Pressure to Mean Arterial Blood Flow is a measure of the resistance created by the blood vessel's contractility state.

$$SVRI = \frac{MAP - LVEDP}{CI} * 80/BSA$$

where SVRI is the Systemic Vascular Resistance Index, LVEDP is Left Ventrical End Diastolic Pressure, and (MAP−LVEDP) is the arterio-venous pressure difference.

Normal Range of SVRI (resting-supine adults): 1660–2580 dyn.sec.cm$^{-5}$.m²

4. % Maximum Heart Rate=Chronotropy: Maximal Heart Rate is calculated by the regression coefficients devised by K. F. Hossack et al.:

For man=227−1.032 times Age

For woman=206−0.597 times Age

In several graphic representations it is convenient to express Chronotropy as %HR (HR*100/Max HR) for appropriate comparison of different individuals' hemodynamic changes. Normal health/male and female in rest have 40% of the Maximal Heart Rate.

5. Ejection Fraction (EF): Eq. 5

The pumping efficiency of the heart is represented by the Ejection Fraction (EF). More specifically, EF represents the percentage of blood volume ejected from the left ventricle during systole.

EF Ranges:

High 65–80

Normal 50–65

Low 35–50

Poor 20–35

6. End-Diastolic Index (EDI)=PRELOAD

EDI is a measure of Preload, and is calculated as follows:

EDI = SI/EF

EDI is a representative value for the systemic volemic state. Normal End-Diastolic Index (relaxing-supine adults): 60–110 ml/m²

7. Acceleration Index (Eq. 4)

ACI is the calculation of the initial speed of the aortic blood flow in the first 20 milliseconds after the opening of the aortic valve at the beginning of the systole. Because at this time other factors (such as systemic peripheral resistance) do not influence this initial speed of blood flow, this acceleration closely reflects the true inotropic state of the left myocardium.

Accepted normal ranges for males are 0.7–1.5 sec$^{-2}$, and for females, are 0.9–1.7 sec$^{-2}$.

8. Left Cardiac Work Index (LCWI):

LCWI represents the physical work the left ventricle has to expend and is proportional to the myocardial $VO_2$ (Oxygen Consumption).

$$LCWI = (MAP-LVEDP)*CI*0.0144$$

where

LCWI is Left Cardiac Work Index [kg.m/m²]

LVEDP is Left Ventricular End Diastolic Pressure (MAP-LVEDP) is pump's pressure contribution 0.0144 is a constant of proportionality.

Normal Left Cardiac Work Index (resting-supine adults): 3.3–5.3 Kg. m/m²

9. Oxygen Delivery Index ($DO_2I$)

$DO_2I$ is the Global Oxygen delivered according to the Hemoglobin content in the amount of blood of the indexed global flow, calculated as:

$$DO_2I = CI \times CaO_2$$

where $DO_2I$ is Global Oxygen Delivery Index [ml/min/m$^2$], CI is the Cardiac Index, $CaO_2 = [\text{Hemoglobin}] \times SaO_2 * 1.34$ (Hemoglobin in mg/liter), $SaO_2$ is the Arterial Oxygen Saturation level in %, 1.34 is a constant of proportionality (ml Oxygen/gram of Hemoglobin). $SaO_2$ fluctuates in a narrow range (from 94–98%) if the patient has a healthy lung function, therefore, for purposes of the calculation, it can be considered constant, similarly to Hemoglobin. The only real variable in this equation, reflecting changes in Oxygen delivery in the equation, is the Cardiac Output. Normal $DO_2I$ (for resting-supine adults) is 570–795 $O_2$ ml/min/m$^2$ for males and 480–670 $O_2$ ml/min/m$^2$ for females.

10. Mean Arterial Blood Pressure (MAP):

To maintain a physiologically optimal oxygenated Blood supply for the vital organs, such as the brain and the heart, a constant opening blood pressure MAP is required, and this pressure is maintained by a cascade of very sophisticated biofeedbacks. MAP is estimated as Diastolic Blood Pressure+⅓ Pulse Pressure.

Normal MAP: (Age and Sex dependent)

males: 84–100 mmHg females: 81–97 mmHg

11. Left Ventricular End Diastolic Pressure (LVEDP) (Eq. 12)

LVEDP, also known as Left Ventricular Filling Pressure is analogous to the Mean Pulmonary Capillary "Wedge" Pressure in the absence of Mitral Valve Disease or Pulmonary Hypertension. The Noninvasive Hemodynamic Analyzer directly computers the LVEDI. The corresponding LVEDP can be calculated by plotting the logarithmic value of LVEDI against the LVEDP.

Normal LVEDP: (age and sex dependent) between 4–12 mmHg

12. Maximal Oxygen Consumption ($VO_2$) (Eq. 13)

This parameter represents the functional limits of the cardiopulmonary system and equals the product of CO*(a–$vO_2$). Since the maximal a–$vO_2$ difference behaves as a constant and CO is calculated by the Noninvasive Hemodynamic Analyzer, an estimate of $VO_2$ can be continuously computed by using the approximate difference of 1.5 a–$vO_2$ vol % for the equation between Rest (~40% Max HR) and 100% Heart Rate (+the average resting value a–$vO_2$). $VO_2$ is also frequently expressed in METs. MET represents 3.5 ml of $O_2$/kg/min, which is about the amount of Oxygen required in resting state.

Referring to FIG. 15, an embodiment of the hemodynamic analyzer according to the present invention is shown. The apparatus includes a microcomputer—capable of handling all algorithmic computations resulting in a complete hemodynamic profile digitally and in graphic form. The results are displayed on an LCD Screen, or are printed out. The computer has a screen 1 and keyboard 5. The analyzer also includes arrhythmia light 2, pulse wave monitor 3, data input 4 (SBP-DBP & HR), heart rate panel 6, % heart rate panel 7, continuous heart rate input 8, and on/off switch 9.

The hemodynamic analyzer analyzes static and dynamic parameters as patient's data and variable hemodynamic inputs, and computes hemodynamic parameters with digital and graphic output, including a hardcopy printout. The apparatus preferably includes an oscillometric blood pressure instrument, featuring an internal compressor that automates cuff inflation. Test sequelae are incorporated into computer-based procedure to obtain systolic & diastolic blood pressure and heart rate. The apparatus also includes a heart rate detector (an automatic arrhythmia selector) for missed beats, premature ventricular contraction, etc., and three monitoring setups: a separate electroluminescent display for visualization of pulse pattern, and continuous displays for actual heart rate and % heart rate.

Optionally, an arterial oxygen saturation monitor is included to provide an exact calculation for the oxygen delivery index, which is important during a major operative procedure and/or when patient does not have normal pulmonary function.

Significantly, the apparatus can be changed to an invasive apparatus by applying an arterial pressure transducer, thus producing a continuous, on-line hemodynamic analyzer.

The programs operating in the microcomputer may include three different programs which run instantaneously according to the input data. The first two programs are resting state programs, performing calculations for supine and upright positions, respectively, for diagnosing and treating hypertension, congestive heart failure and other hemodynamic compromised states.

Figure 1:
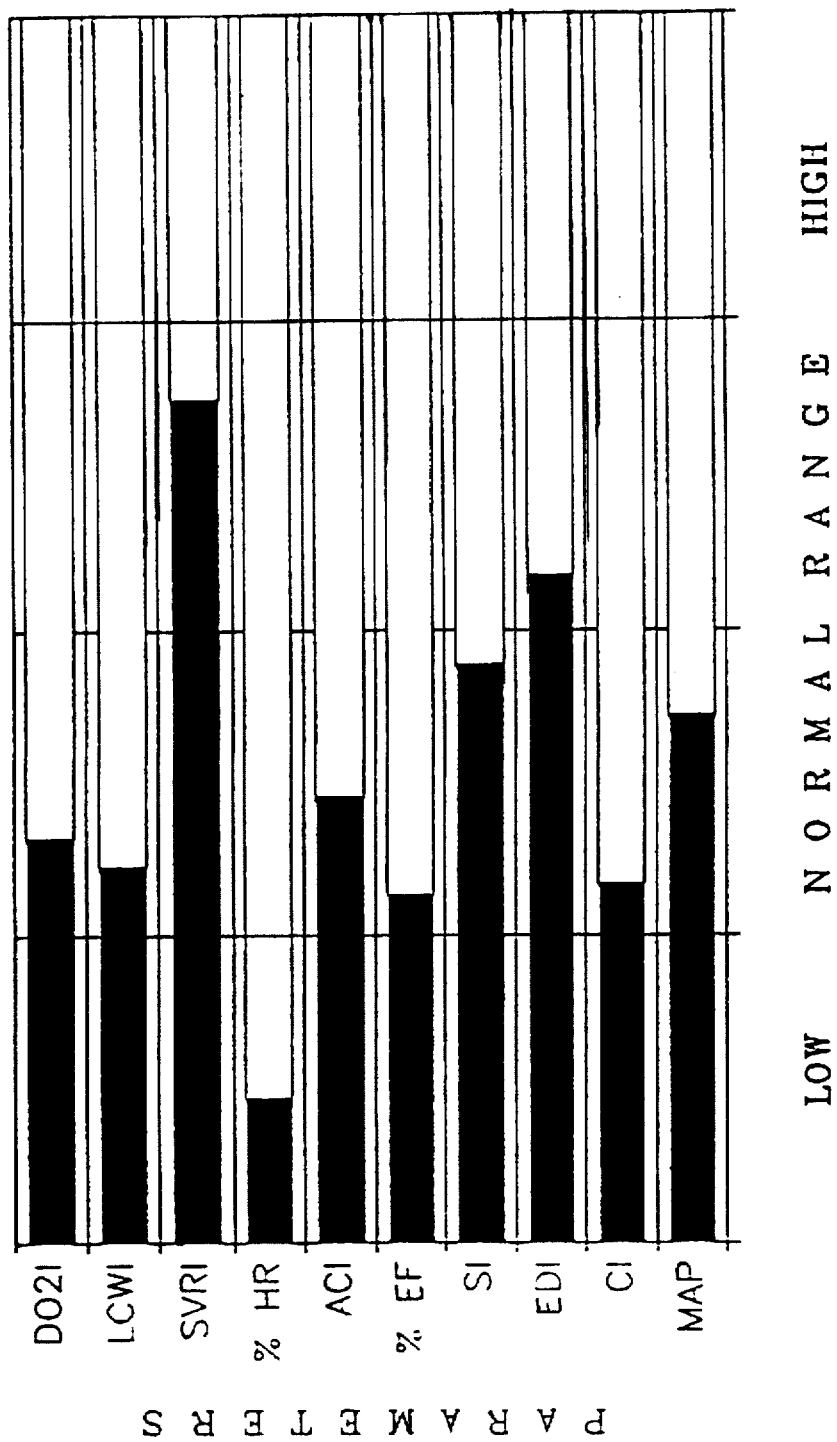
FIG. 1 is a diagnostic graph produced by the present system, showing ten hemodynamic values for a resting-supine position. The graph provides a hemodynamic profile and the ten calculated values can be evaluated according to differences from normal ranges and represented as Normal, Low, or High. By this arrangement an immediate diagnostic summary can be achieved.
Figure 2:
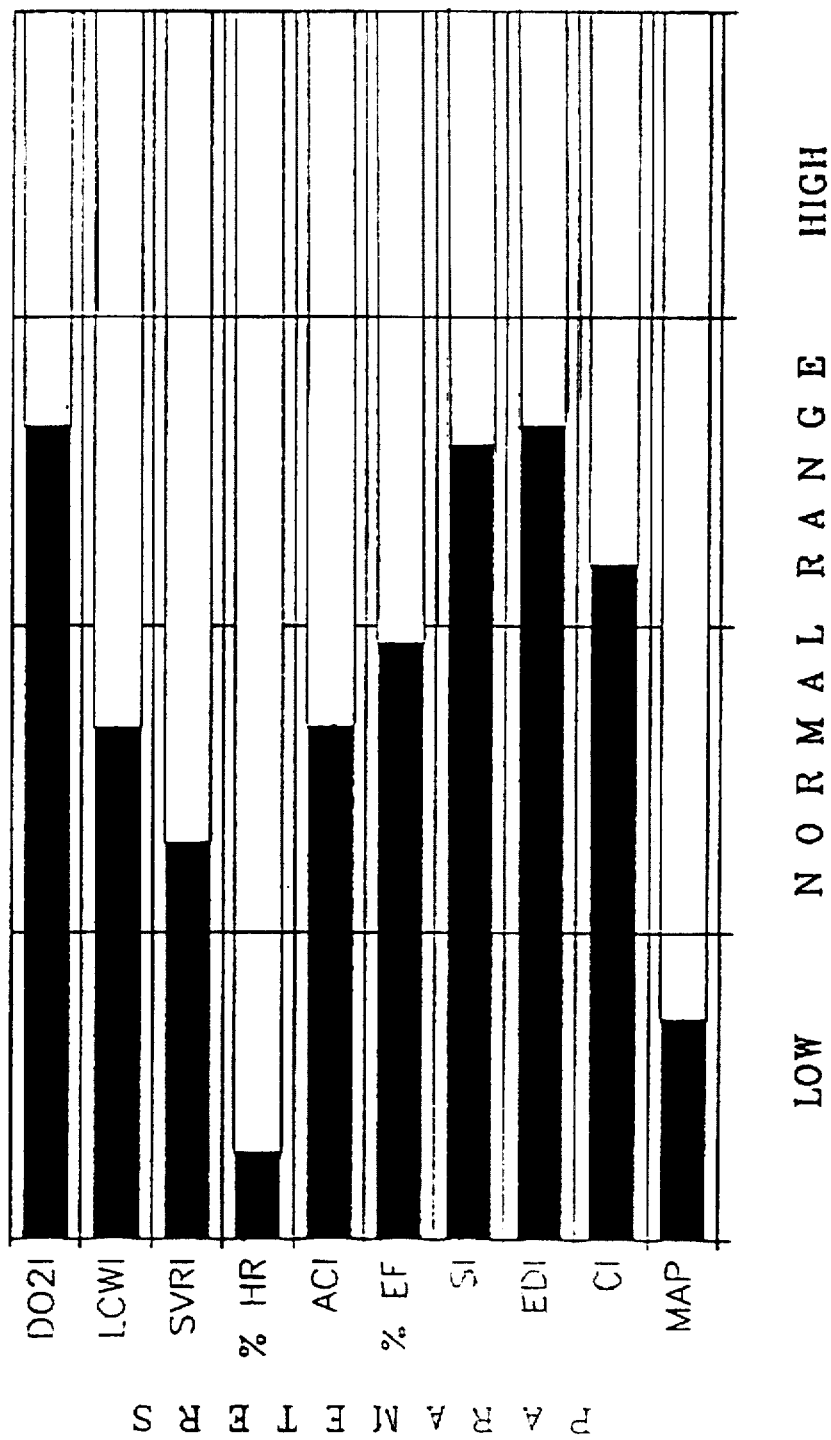
FIG. 2 is a diagnostic graph similar to that of FIG. 1 but showing the ten hemodynamic values measured in a resting-upright position.
Figure 3:
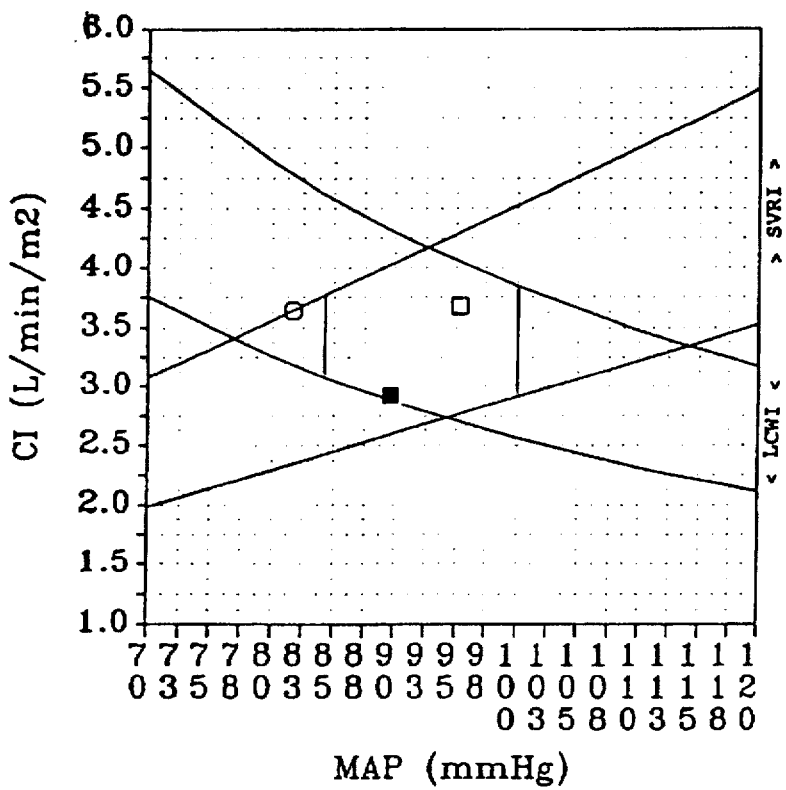
FIG. 3 is a therapeutic indication graph produced by the present system, showing a plot of the Cardiac Index against the Mean Arterial Pressure values in the Resting-Supine and Upright positions. The graph also contains two calculated hemodynamic parameters: the Ideal Systemic Vascular Resistance Indices (straight diagonal line) and the Ideal Left Cardiac Work Indices (curved diagonal line) with ±20% ranges. The upper line of the Systemic Vascular Resistance Index represents vasodilatation and its lower line depicts vasoconstriction. The upper and lower curves of the Left Cardiac Work Index demonstrate increased or decreased Myocardial Oxygen Consumption as related to the Mean Arterial Pressure. The Upright-Ideal CI/MAP value is calculated according to the age and sex of the patient. The actual values of the Supine/Upright CI/MAP positions can be referred to the ideal value and according to their place on the graph, therapeutic correction can be made.
Figure 4:
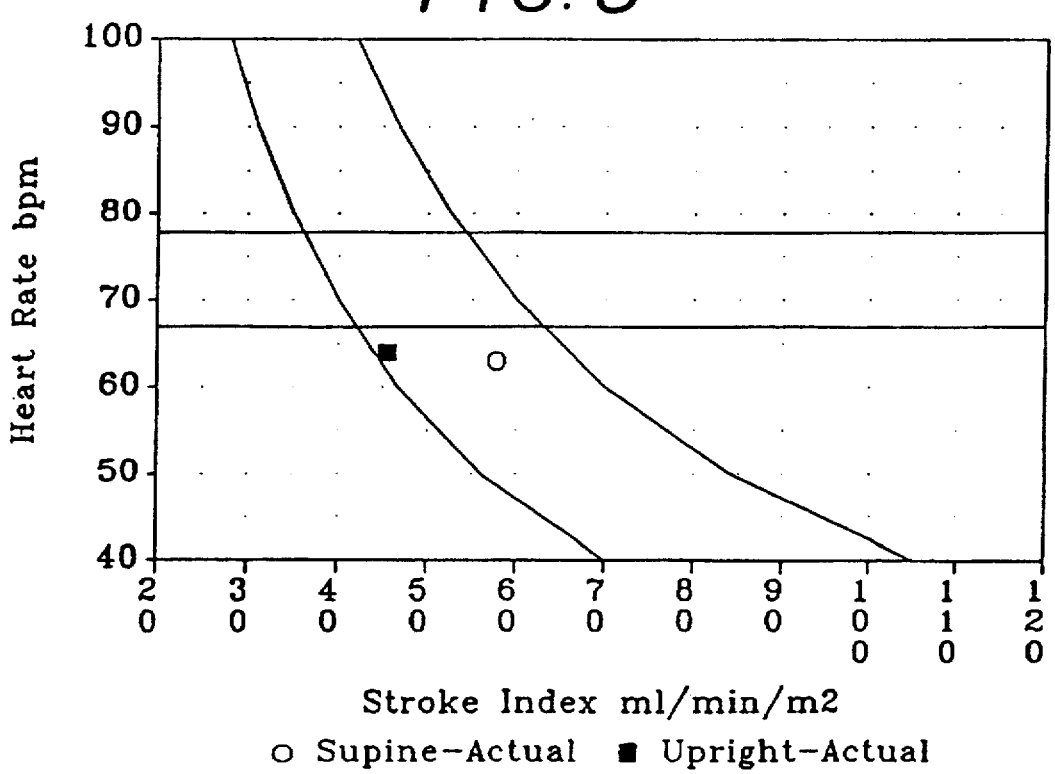
FIG. 4 is a diagnostic graph produced by the inventive system, showing the correlation between Ideal Resting Heart Rate (in the range of 37–43% of the Maximal Heart Rate) and the Ideal Range of Stroke Index.
Figure 5:
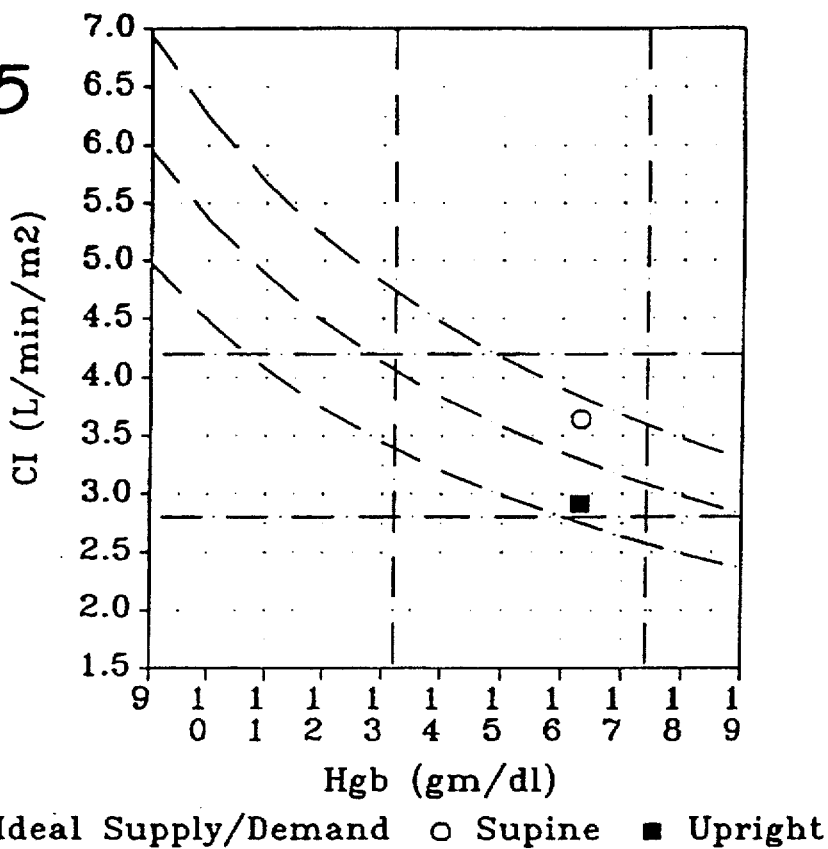
FIG. 5 is a diagnostic graph produced by the inventive system showing Cardiac Index plotted against Hemoglobin content. Assuming 95% arterial $O_2$ Saturation, the curved lines represent the range of normal Oxygen Delivery Index. This graph can be read easily to provide information about Oxygen Supply and Demand.
Figure 6:
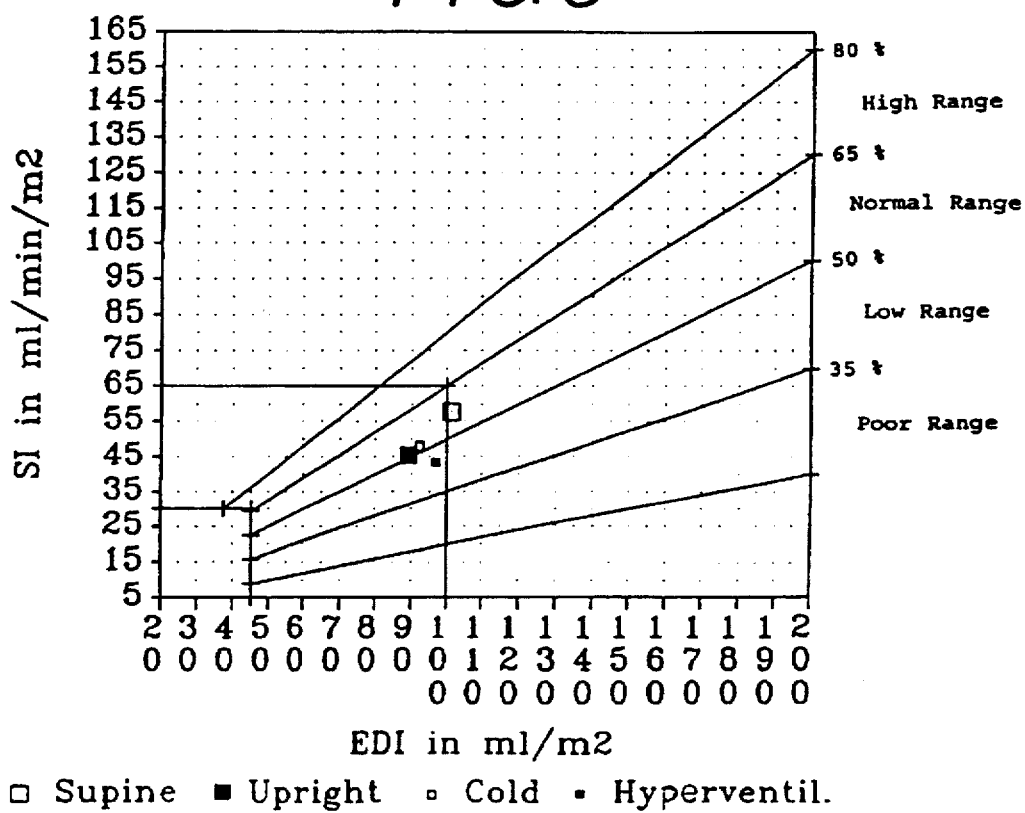
FIG. 6 is a diagnostic graph produced by the inventive system plotting the Stroke Index against the End Diastolic Index. The resultant ratio can be depicted at the right as the % Ejection Fraction, one of the most important indices of the Left Ventricle Efficiency.

The resting state programs preferably produce graphs for elucidating interactions/interconnections of a hemodynamic profile. The graphs may include diagnostic directions of the hemodynamic analysis—supine position (see Example); diagnostic directions of the hemodynamic analysis—upright position (see Example); hemodynamic profile in resting—supine position (FIG. 1); hemodynamic profile in resting—upright position (FIG. 2); therapeutic indication: representing the ideal and actual plotted points of cardiac index (CI) & mean arterial blood pressure (MAP) with calculations of left cardiac work index (LCWI) & systemic vascular resistance index (SVRI) (FIG. 3); correlation between stroke index (SI) and heart rate in connection to cardiac index (CI) (FIG. 4); oxygen supply and demand in resting—supine and upright positions (FIG. 5); cardiac efficiency (%EF) in resting by a modified Starling Curve: stroke index (SI) is plotted against end diastolic index (EDI) (FIG. 6); psychosomatic stress test: representing hemodynamic reactivities after applying cold stress and hyperventilation and graphically illustrating hemodynamic changes; mean arterial pressure (MAP), stroke index (SI), % heart rate, systemic vascular resistance index (SVRI) (FIG. 7); and preload (EDI), cardiac index CI), myocardial contractility (ACI) and afterload (SVRI) (FIG. 8).

A third program performs calculations for an exercise stress test, representing detailed hemodynamic interactions using the following graphs: ideal and actual blood pressure (SBP, MAP & DBP) responses with the corresponding % heart rate changes (FIG. 9); correlation between SI and % of the maximum heart rate during exercise (FIG. 10); composite graph of hemodynamic changes during exercises, participating LCWI, SVRI, according to myocardial contractility (ACI) changes (FIG. 11); cardiac efficiency (%EF) changes during exercise as a manifestation of EDI changes resulting in SI responses (FIG. 6); and a Starling Curve during exercise comparing responses of SI to myocardial contractility changes. (FIG. 12).

Referring again to FIG. 15, after obtaining a continuous regular Heart Rate pattern, operation begins after typing 9 obligatory and 2 optional data for single or multiple measurements. SBP, DBP & HR data are collected automatically whenever the test procedure requires the registration. SBP, DBP and HR can be typed in if desired. If an exercise study is performed, % Heart rate panel 7 helps to select the appropriate exercise level at about 40, 60 and 80% Heart Rates. An exercise study can be performed if arrhythmia is not present.

The age of the patient is used by the algorithm and in the embodiment disclosed, is restricted to ages 18–70.

The absolute limitation of any cardiac output measurement is heart rate irregularity. In the present invention— three regular electrodes are applied on the chest and the hemodynamic analyzer by the pulse wave monitor which continuously validates the ongoing test.

The computer algorithms used for computing ideal and actual hemodynamic parameters will now be described in detail with reference to FIGS. 19a and 19b. As illustrated in FIG. 19a and FIG. 19b the computer is programmed with two parallel algorithms 300 & 500 including an entry block 302 wherein the program begins.

The algorithm begins operating only after the operator decides that no significant irregularities are present by judging the pulse pattern of the pulse wave monitor.

Thereafter, the program manually requests the block of static characteristics 310 (including the patient's Name/Identification number, Date of test, Date of Birth, Sex, height (in inches), and weight (in lbs). When an interrupt occurs for Hemoglobin, actual Hemoglobin if known can be typed in or if is unknown, the average Hemoglobin will be computed according to sex (M=15.3, F=12.9).

Thereafter, the algorithm enters block 330 of FIG. 19a: Dynamic Parameters, in which the computer inputs are provided either as a direct digital input from an automated blood pressure measuring system as discussed earlier, or indirectly as harvested information, manually. The inputs provided are systolic blood pressure, diastolic blood pressure, and corresponding heart rate. After the computer receives both static and dynamic parameters, two parallel cascades of algorithms will be initiated.

In FIG. 19b, algorithms for computing the ideal Stroke volume and the corresponding hemodynamic parameters are presented in five distinguished blocks.

In the first process block in calculating ideal parameters, the heart rate values, such as ideal Maximal HR (block 502) and the ideal % Heart Rates of Maximal Heart Rate, are calculated.

These calculations lead to the second process block of ideal Pressure Values: ideal pressure rate products (block 512), ideal systolic blood pressure (block 514), ideal mean arterial pressure (block 576), and ideal diastolic blood pressure (block 518).

After these computations are fulfilled intermediary parameters of the third process block are obtained: ideal heart rate ratios (block 522), ideal pulse pressure ratios (block 524), and ideal pulse pressure values (block 526) all at 40 to 100% of maximal heart rates.

In the fourth process block as described earlier with reference to Equations 3a and 3b, the ideal stroke volume calculation with its all associated correction factors is presented. At this point of computation, the adjustment(block 574), obtained (block 574), which is used in the parallel cascade of algorithm 300 for the actual stroke volume calculation in Equations 3a and 3b. In both parallel algorithms, ideal and actual, after obtaining the stroke volume levels, the twelve final hemodynamic parameters can be calculated by known, accepted, general physiological equations, with the exception of two parameters, namely: ideal and actual acceleration indices (Eq. 4), ideal and actual % ejection fractions (Eq. 5), and ideal and actual left ventricular end diastolic pressure (Eq. 12) as described earlier. The last block of final hemodynamic parameters consists of the following 12 hemodynamic participants: 380 and 550.

| | |
|---|---|
| 1. MEAN ARTERIAL BLOOD PRESSURE | 384 |
| 2. CARDIAC INDEX | 392 |
| 3. END DIASTOLIC INDEX | 396 |
| 4. STROKE INDEX | 372 |
| 5. % EJECTION FRACTION | 388 |
| 6. ACCELERATION INDEX | 386 |
| 7. % HEART RATE OF MAX. HR | 382 |
| 8. SYSTEMIC VASCULAR RESISTANCE INDEX | 394 |
| 9. LEFT CARDIAC WORK INDEX | 398 |
| 10. OXYGEN DELIVERY INDEX | 400 |
| 11. LEFT VENTRICULAR END DIASTOLIC PRESSURE | 402 |
| 12. MAXIMAL OXYGEN CONSUMPTION | 404 |

FIG. 20 is a flowchart showing the operative steps to compute the hemodynamic profile in the present invention. As illustrated in FIG. 20, the operation starts placing the ECG electrodes on the chest (block 204) and blood pressure cuff preferably on the left arm (block 206) according to the pre-arrangement order (block 262). After static parameters are typed in (block 208), the question: "Is arrhythmia present?" (block 210) will be answered. If answer is yes, computation will not start, and control is transferred to exit the program (block 212).

If arrhythmia is not present, the first question, referring to one of the three test types—will be asked: "Is this a test in RESTING?" (block 214). If the answer is yes, in block 218 the dynamic parameters, systolic and diastolic blood pressures and heart rate, will be received by computer 260 directly, as an analog computer input or manually by typing.

If the next question is answered by yes: "Do you want a STRESS TEST?" (block 222) steps of Cold Stress Application (block 226), Hyperventilation (block 232) and Upright Position (block 242) will be initiated by receiving their Dynamic Parameters in blocks 228, 234 and 244.

After the yes answer of the next question: "Is this test an EXERCISE EVALUATION?" in block 238, two sets of Dynamic Parameters (blocks 250 and 256) are collected preferably at 60 and 80% Heart Rate. By this sequence of steps three types of hemodynamic evaluation can be obtained in block 300:

1. Hemodynamic Profile in Resting
2. Psychosomatic Stress Testing and
3. Exercise Stress Testing with complete digital and graphic representations.

The apparatus of the present invention was used to monitor a young, healthy patient and determine his hemodynamic profiles, both in Resting and in an exercise stress test. The patient was exercising regularly and had no cardiopulmonary history. The following information was obtained:

Static Parameters:

| | |
|---|---|
| Name: | D.L. |
| ID No.: | 2617 |
| Sex: | Male |
| Date of Birth: | 6/12/57 |
| Date of Examination: | 03/20/93 |
| Height: | 71" |
| Weight: | 170 lbs |
| Hemoglobin: | 15.3 g/dl |

Dynamic Parameters:

| Testing State | Rest | | Exercise | |
| --- | --- | --- | --- | --- |
| Testing Type: | Supine | Cold | 1st | 2nd |
| Systolic Blood Pressure | 121 | 122 | 148 | 163 |
| Diastolic Blood Pressure | 72 | 74 | 66 | 58 |
| Heart Rate | 63 | 70 | 112 | 156 |

FIGS. 23a and 23b show the data collected for the patient in the resting (supine and upright) positions. FIG. 23c shows the data collected during the exercise stress test. The examples in FIGS. 1–6 and 13 are graphical representations of the collected resting data for this patient, while FIGS. 9–12 and 14 graphically represent the stress test exercise data for the patient.

An evaluation of the validity of the stroke volume/cardiac output measurement of the present invention has been conducted. It is generally recognized that all invasive or noninvasive cardiac output methods have a biological error of measurement of 10–15%. Adding operator errors and instrument calibration errors, the overall accuracy is never better than ±20% from the actual cardiac output value.

The correct way, therefore, to assess the agreement between any two cardiac output methods is by using a scattergram and plotting +20% confidence band lines on it (because there is no existing calibration standard having absolute accuracy).

The method of the present invention was evaluated by calculating cardiac output of 50 men and women. For each person, four measurements were obtained: measurements in supine and upright positions respectively (resting), and two measurements in an upright position during treadmill exercise. The data of 200 points were plotted against simultaneously measurements obtained with the noninvasive bio-impedance method of the BoMed NCCOM3 instrument, as shown in FIG. 21.

An excellent correlation was obtained with 97% of the points scattered between the ±20% Confidence Level Bands (88% between ±15% CLB and 75% between ±10% CLB), as shown by the analysis in FIG. 22.

Thus, the reader will see that the noninvasive hemodynamic sequential analysis of the present invention is a highly reliable and statistically proven method useful in calculating cardiovascular parameters including cardiac output.

The present invention permits the user to compute a complete, real-time Hemodynamic Profile in Rest and Exercise. It provides the user with not only a digital, but also an instantaneous graphical display with the ability to print out hemodynamic changes. The invention also allows the user a means to screen a large number of people for cardiovascular conditions in the most economical, fast and accurate way.

The invention also opens a new, direct approach for the medical profession to investigate and/or regulate hemodynamic changes following drug-therapy of different diseases and/or medical conditions (e.g., Hypertension, Congestive Heart Failure, Postoperative Managements, etc.).

The inexpensive diagnostic, therapeutic and prognostic application of the present invention could significantly influence the economy of medical care to reduce the health care cost of these aspects.

Although the description above contains many specificities, these should not be understood as limiting the scope of this Invention. What has been shown are preferred embodiments of the present invention.

I claim:

1. A computerized apparatus for electronically determining cardiac parameters in a human patient in the presence of a regular heart rate pattern, comprising:

computing means for receiving and storing a set of input parameters including a single actual heart rate value, a single actual systolic blood pressure value and a single actual diastolic blood pressure value, and sex, weight, age and height of the patient;

calculating means associated with the computing means for generating an estimate of actual cardiac stroke volume from:
(a) said single heart rate value,
(b) blood pressure information consisting only of said single systolic and diastolic blood pressure values, and
(c) said sex, weight, age, and height of the patient; and output means connected to the calculating means for providing an output to an operator representing said estimate of actual cardiac stroke volume.

2. The apparatus of claim 1 further comprising monitoring means connected to the computing means for noninvasively obtaining said single actual heart rate value and single actual systolic and diastolic blood pressure values and transmitting these values to the computing means.

3. The apparatus of claim 1 further comprising display means connected to the calculating means for generating a graphical hemodynamic profile output.

4. The apparatus of claim 3 wherein the calculating means further includes means for determining mean arterial blood pressure, cardiac index, end diastolic index, stroke index, % ejection fraction, acceleration index, percent of maximum heart rate, systemic vascular resistance index, left cardiac work index, and oxygen delivery index, and said display means further includes means for providing the graphical hemodynamic profile output in the form of a bar graph showing mean arterial blood pressure, cardiac index, end diastolic index, stroke index, % ejection fraction, acceleration index, percent of maximum heart rate, systemic vascular resistance index, left cardiac work index, and oxygen delivery index.

5. The apparatus of claim 3 wherein the display means includes means for showing a normal range for parameters displayed in the hemodynamic profile.

6. The apparatus of claim 1 wherein the calculating means further includes:

percent heart rate determining means for determining a maximum heart rate for the patient based on said input parameters and calculating a % heart rate based on the actual heart rate and the maximum heart rate;

ideal blood pressure determining means for calculating an ideal systolic and an ideal diastolic blood pressure for the patient at the % heart rate;

preliminary ideal stroke volume determining means for calculating preliminary ideal stroke volume based on the ideal systolic blood pressure and the ideal diastolic blood pressure;

preliminary ideal cardiac output determining means for calculating a preliminary ideal cardial output value based on the preliminary ideal stroke volume;

indexing means for indexing said preliminary ideal cardiac output value to an ideal body surface area for the patient to obtain a preliminary ideal cardiac index, and adjusting said preliminary ideal cardiac index according to patient age to obtain an ideal cardiac index; and actual cardiac stroke volume determining means for estimating an actual cardiac stroke volume based on the actual heart rate, blood pressure, and the difference between the ideal cardiac index and preliminary ideal cardiac index, and for providing said estimated actual cardiac stroke volume to said output means.

7. The apparatus of claim 6 wherein the calculating means further includes means for determining whether the patient heart rate is less than 40% of the maximal heart rate, and if so, compensating for the decreased heart rate by correspondingly increasing the calculated value of the stroke volume.

8. The apparatus of claim 1 further comprising means for calculating a percent ejection fraction by a two step process wherein in the first step an Ideal ejection fraction is calculated and adjusted to heart rate according to
$EF_{ideal}=((\%Heart\ Rate-Actual-40)*0.1)+57$ where %HR-Actual=HR*100/Max HR and 57 is the theoretical average ejection fraction; and in the second step the actual percent ejection fraction is calculated according to:

$$ActualEF = \sqrt{\frac{PP-A*HR-A}{PP-I*HR-I} *EF-I}$$

9. The apparatus of claim 1 wherein the calculating means further includes means for generating a graphical output relating at least two additional hemodynamic parameters, and further comprising display means for displaying said graphical output to facilitate diagnosis.

10. The apparatus of claim 9 wherein the display means further includes means for displaying an ideal relationship between said at least two hemodynamic parameters in addition to a measured relationship.

11. A computerized apparatus for electronically determining cardiac parameters in a human patient in the presence of a regular heart rate pattern, comprising:

computing means for receiving and storing a set of input parameters including a single actual heart rate value, single actual systolic and diastolic blood pressure values, and sex, weight, age and height of the patient, said computing means further comprising means for receiving and storing a hemoglobin value;

calculating means associated with the computing means for generating an estimate of actual cardiac stroke volume from said single heart rate value, said single systolic and diastolic blood pressure values, and said sex, weight, age, and height of the patient, wherein said estimate of actual cardiac stroke volume is calculated based only on said single heart rate value, said single systolic and diastolic blood pressure values, said sex, weight, age, and height of the patient, and said hemoglobin value; and output means connected to the calculating means for providing an output to an operator representing said estimate of actual cardiac stroke volume.

12. A computer program for electronically determining cardiac parameters in a human patient in the presence of a regular heart rate pattern, comprising a recording medium encoded with computer program codes, said codes defining:

computing means for receiving and storing a set of input parameters including a single actual heart rate value, a single actual systolic blood pressure value and a single actual diastolic blood pressure value, and sex, weight, age and height of the patient;

calculating means associated with the computing means for generating an estimate of actual cardiac stroke volume from:
(a) said single heart rate value,
(b) blood pressure information consisting only of said single systolic and diastolic blood pressure values, and
(c) said sex, weight, age, and height of the patient;

output means connected to the calculating means for providing an output to an operator representing said estimate of actual cardiac stroke volume; and display means associated with the calculating means for receiving output therefrom and generating a graphical hemodynamic profile output.

13. The computer program of claim 12 herein the computing means further comprises means for receiving and storing a hemoglobin value, wherein said estimate of actual cardiac stroke volume is calculated based only on said single heart rate value, said single systolic and diastolic blood pressure values, said sex, weight, age, and height of the patient, and said hemoglobin value.

14. The computer program of claim 12 wherein the calculating means further includes:

percent heart rate determining means for determining a maximum heart rate for the patient based on said input parameters and calculating a % heart rate based on the actual heart rate and the maximum heart rate;

ideal blood pressure determining means for calculating an ideal systolic and an ideal diastolic blood pressure for the patient at the % heart rate;

preliminary ideal stroke volume determining means for calculating preliminary ideal stroke volume based on the ideal systolic blood pressure and the ideal diastolic blood pressure;

preliminary ideal cardiac output determining means for calculating a preliminary ideal cardial output value based on the preliminary ideal stroke volume;

indexing means for indexing said preliminary ideal cardiac output value to an ideal body surface area for the patient to obtain a preliminary ideal cardiac index, and adjusting said preliminary ideal cardiac index according to patient age to obtain an ideal cardiac index; and actual cardiac stroke volume determining means for estimating an actual cardiac stroke volume based on the actual heart rate, blood pressure, and the difference between the ideal cardiac index and preliminary ideal cardiac index, and for providing said estimated actual cardiac stroke volume to said output means.

15. The computer program of claim 14 wherein the calculating means further includes means for determining whether the patient heart rate is less than 40% of the maximal heart rate, and if so, compensating for the decreased heart rate by correspondingly increasing the calculated value of the stroke volume.

16. The computer program of claim 12 further comprising means for calculating a percent ejection fraction by a two step process wherein in the first step an Ideal ejection fraction is calculated and adjusted to heart rate according to
$EF_{ideal}=((\%Heart\ Rate-Actual-40)*0.1)+57$ where %HR-Actual=HR*100/Max HR and 57 is the theoretical average ejection fraction; and in the second step the actual percent ejection fraction is calculated according to:

$$ActualEF = \sqrt{\frac{PP-A*HR-A}{PP-I*HR-I} *EF-I} \ .$$

* * * * *